(12) United States Patent
Lilga et al.

(10) Patent No.: US 9,434,659 B2
(45) Date of Patent: Sep. 6, 2016

(54) CONVERSION OF 2,3-BUTANEDIOL TO BUTADIENE

(71) Applicant: Battelle Memorial Institute, Richland, WA (US)

(72) Inventors: Michael A. Lilga, Richland, WA (US); John G. Frye, Jr., Richland, WA (US); Suh-Jane Lee, Richland, WA (US); Karl O. Albrecht, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 65 days.

(21) Appl. No.: 14/607,871

(22) Filed: Jan. 28, 2015

(65) Prior Publication Data

US 2015/0218062 A1 Aug. 6, 2015

Related U.S. Application Data

(60) Provisional application No. 61/935,050, filed on Feb. 3, 2014.

(51) Int. Cl.
| | | |
|---|---|---|
| *C07C 1/24* | (2006.01) | |
| *C07C 29/60* | (2006.01) | |
| *B01J 19/00* | (2006.01) | |
| *C07C 1/207* | (2006.01) | |
| *C07C 49/203* | (2006.01) | |
| *C07C 1/30* | (2006.01) | |

(52) U.S. Cl.
CPC .................. *C07C 1/24* (2013.01); *B01J 19/00* (2013.01); *C07C 29/60* (2013.01); *C07C 1/2078* (2013.01); *C07C 1/30* (2013.01); *C07C 49/203* (2013.01); *C07C 2521/04* (2013.01); *C07C 2521/06* (2013.01); *C07C 2523/02* (2013.01); *C07C 2523/08* (2013.01); *C07C 2523/10* (2013.01); *C07C 2527/167* (2013.01); *C07C 2529/40* (2013.01); *C07C 2529/70* (2013.01)

(58) Field of Classification Search
CPC ...... C07C 49/203; C07C 1/30; C07C 1/2078
USPC .......................................... 568/383; 585/538
See application file for complete search history.

(56) References Cited

U.S. PATENT DOCUMENTS

| | | | |
|---|---|---|---|
| 2,400,409 | A | 5/1946 | Hale et al. |
| 4,927,979 | A | 5/1990 | Yamagishi et al. |
| 6,479,713 | B1 | 11/2002 | Werpy et al. |
| 6,670,300 | B2 | 12/2003 | Werpy et al. |
| 6,677,385 | B2 | 1/2004 | Werpy et al. |
| 6,706,893 | B2 | 3/2004 | Werpy et al. |
| 6,841,085 | B2 | 1/2005 | Werpy et al. |
| 6,982,328 | B2 | 1/2006 | Werpy et al. |
| 7,038,094 | B2 | 5/2006 | Werpy et al. |
| 7,186,668 | B2 | 3/2007 | Werpy et al. |
| 7,199,250 | B2 | 4/2007 | Werpy et al. |
| 8,937,202 | B2 | 1/2015 | Frye et al. |
| 2007/0191584 | A1 | 8/2007 | Ito et al. |
| 2011/0207972 | A1 | 8/2011 | Brown et al. |

FOREIGN PATENT DOCUMENTS

| | | |
|---|---|---|
| SU | 429050 | 5/1974 |
| WO | WO 2012/174439 | 12/2012 |

OTHER PUBLICATIONS

Abe et al., "Vapor-phase catalytic dehydration of terminal diols," *Catalysis Today*, (2011) 164: 419-424.
Bhattacharyya et al., "One-Step Catalytic Conversion of Ethanol to Butadiene in a Fluidized Bed," *Ind. Eng. Chem. Process Des. Dev.*, (1963) 2(1): 45-51.
Davis, "Dehydration and Dehydrogenation of 2-Octanol by Thorium Oxide," *Journal of Catalysis*, (1972) 25: 81-92.
Davis, "Catalytic Conversion of Alcohols, VI. Selectivity of Indium Oxide," *Journal of Catalysis*, (1978), 52: 435-444.
Dabbagh et al, "Catalytic Conversion of Alcohols: Olefin Selectivity from 2,4,4-Trimethyl-2-pentanol using metal oxide catalysts selective for Hofmann or Saytzeff Elimination," *J. of Molecular Catalysis*, (1988) 47: 123-127.
International Search Report and Written Opinion, dated May 6, 2015, issued in corresponding International Application No. PCT/US2015/013312.
Lundeen et al., "Selective Catalytic Dehydration of 2-Alcholos; a New Synthesis of 1-Olefins," *J. Am. Chem. Soc.*, (1963), 85:2180-2181.
Lundeen et al., "Selective Catalytic Dehydration. Thoria-Catalyzed Dehydration of Alcohols," *J. Org. Chem.*, (1967), 32(11):3386-3389.
Morell et al., "Conversion of 2,3-Butylene Glycol to 1,3-Butadiene by Pyrolysis of Diacetate," *Industrial and Engineering Chemistry*, (1945) 37(9): 877-884.
Sato et al., "Catalytic reaction of 1,3-butanediol over rare earth oxides," *Applied Catalysis A: General* (2007) 328: 109-116.
Sato et al., "Selective Dehydration of Alkanediols into Unsaturated Alcohols over Rare Earth Oxide Catalysis," *ACS Catalysis*, (2013) 3:721-734.

(Continued)

*Primary Examiner* — Elvis O Price
(74) *Attorney, Agent, or Firm* — Klarquist Sparkman, LLP

(57) ABSTRACT

A composition comprising 2,3-butanediol is dehydrated to methyl vinyl carbinol and/or 1,3-butadiene by exposure to a catalyst comprising (a) $M_xO_y$ wherein M is a rare earth metal, a group IIIA metal, Zr, or a combination thereof, and x and y are based upon an oxidation state of M, or (b) $M^3{}_a(PO_4)_b$ where $M^3$ is a group IA, a group IIA metal, a group IIIA metal, or a combination thereof, and a and b are based upon the oxidation state of $M^3$. Embodiments of the catalyst comprising $M_xO_y$ may further include $M^2$, wherein $M^2$ is a rare earth metal, a group IIA metal, Zr, Al, or a combination thereof. In some embodiments, 2,3-butanediol is dehydrated to methyl vinyl carbinol and/or 1,3-butadiene by a catalyst comprising $M_xO_y$, and the methyl vinyl carbinol is subsequently dehydrated to 1,3-butadiene by exposure to a solid acid catalyst.

20 Claims, 2 Drawing Sheets

(56) References Cited

OTHER PUBLICATIONS

Schniepp et al., "Pilot-Plant Conversion of 2,3-Butylene Glycol Diacetate to 1,3-Butadiene," *Industrial and Engineering Chemistry*, (1945) 37(9): 884-889.

Segawa et al., "Vapor-phase catalytic reactions of alcohols over bixbyite indium oxide," *Journal of Molecular Catalysis A: Chemical* (2009), 310, pp. 166-173.

Solinas et al., "Doped zirconia catalysts for the dehydration of 4-methylpentan-2-ol.," *Studies in Surface Science and Catalysis*, 140: 175-184, 2001, abstract only.

Takahashi et al., "Synthesis of 3-buten-1-ol from 1,4-butanediol over indium oxide," *Applied Catalysis A: General*, (2010) 383: 134-140.

Winfield, "The Catalytic Dehydration of 2,3-Butanediol to 1,3-Butadiene," *J. Coun. Sci. Indust. Res.*, (1945), pp. 412-423.

Winfield, "The Catalytic Dehydration of 2,3-Butanediol to Budadiene, II. Adsorption Equilibria," *Aust. J. Sci. Res. Series a-Phys. Sci.*, (1950), 3(2): 290-305.

US 9,434,659 B2

CONVERSION OF 2,3-BUTANEDIOL TO BUTADIENE

CROSS-REFERENCE TO RELATED APPLICATION

This claims the benefit of the earlier filing date of U.S. Provisional Application No. 61/935,050, filed Feb. 3, 2014, which is incorporated by reference in its entirety herein.

ACKNOWLEDGMENT OF GOVERNMENT SUPPORT

This invention was made with government support under DE-AC05-76RL01830 awarded by the United States Department of Energy. The government has certain rights in the invention.

FIELD

This disclosure concerns embodiments of catalysts and a method for converting 2,3-butanediol to 1,3-butadiene.

BACKGROUND 1,3-Butadiene (1,3BD) is an important industrial chemical. 1,3-Butadiene is a major component of synthetic rubber, ABS (acrylonitrile-butadiene-styrene terpolymer), and latex. It is an important intermediate in production of the nylon intermediates adiponitrile and hexamethylenediamine. 1,3-Butadiene is also used to make higher value chemicals, such as cycloalkanes, cycloalkenes, 1-octene chloroprene, sulfolane, 4-vinylcyclohexene, cyclooctadiene, and cyclododecatriene. Vinylcyclohexene, for example, can be converted to styrene, which has a market of about 20 billion pounds (about 9 billion kg) per year. 1,3-Butadiene is an important co-monomer of polyethylene with a market size of over 1 billion pounds (over 450 million kg) per year. 1,3BD also can be oligomerized to form dimers, trimers, and tetramers that are useful as fuel components.

2,3-Butanediol (BDO), which may be generated as a product in some fermentation and thermochemical systems, can be used for production of bio-renewable 1,3BD. However, known methods for converting BDO to 1,3BD suffer from several disadvantages, including corrosive reagents, radioactive catalysts, and/or undesirable products. For example, BDO can be esterified with acetic acid to the diacetate, followed by pyrolysis of the diacetate to 1,3BD (Morell, *Industrial and Engineering Chemistry*, 37(9):877-884, 1945). This approach is complicated by the corrosive nature of the acetic acid produced, which necessitates special materials of construction.

A secondary route to 1,3BD starting with BDO is through 2-butenes, which are available either from 2-butanol by dehydration or from the 1,3-dioxolanes by acid catalyzed thermolysis. The butenes can be catalytically dehydrogenated to 1,3BD in the presence of superheated steam as diluent and heating medium (Kearby, *The chemistry of petroleum hydrocarbons*, ed. B. T. Brooks et al., Vol. 2., Reinhold, N.Y., 1955).

Dehydration of BDO is another route to 1,3BD. Dehydration of BDO can proceed by different mechanisms depending upon the catalyst used. Over many catalysts, including catalysts that are Brønsted acids (e.g., alumina, acidic zeolites), the product is methyl ethyl ketone (MEK).

SUMMARY

A feed stream including 2,3-butanediol (BDO) is converted to methyl vinyl carbinol (MVC) and/or 1,3-butadiene (1,3BD) by exposure to a catalyst comprising (a) $M_xO_y$, wherein M is a rare earth metal, a group IIIA metal, Zr, or a combination thereof, and x and y are based upon an oxidation state of M, or (b) $M^3{}_a(PO_4)_b$ where $M^3$ is a group IA, a group IIA metal, a group IIIA metal, or a combination thereof, and a and b are based upon the oxidation state of $M^3$. In some embodiments, the catalyst further includes a dopant $M^2$, wherein $M^2$ is a rare earth metal, a group IA metal, a group IIA metal, a group IIIA metal, Zr, or a combination thereof, and wherein $M^2$ is different than M or $M^3$. In any or all of the above embodiments, the catalyst may be (i) an oxide of In, Al, La, and Zr, (ii) an oxide of Al and Zr, (iii) an oxide of Zr and Ca, (iv) $Tm_2O_3$, (v) $ZrO_2$, (vi) $Sc_2O_3$, or (vii) $In_2O_3$. In any or all of the above embodiments, the catalyst may have a MVC selectivity of at least 20%, a 1,3BD selectivity of at least 20%, or a combined 1,3BD and MVC selectivity of at least 20%. In any or all of the above embodiments, the composition may comprise at least 5 wt % BDO. In any or all of the above embodiments, the catalyst may dehydrate at least 5% of the BDO.

In any or all of the above embodiments, the BDO feed stream may be contacted with the catalyst at a temperature within a range of 250° C. to 700° C., such as a temperature of 250° C. to 400° C. In some embodiments, the feed stream is contacted with the catalyst at ambient pressure.

In any or all of the above embodiments, the feed stream may be contacted with the catalyst by flowing the feed stream over the catalyst or through a catalyst bed comprising the catalyst at a flow rate effective to produce a W/F (catalyst weight (g)/feed flow rate (mol/h)) value within a range of 0.5 to 100 g catalyst·h/mol feed stream, such as a W/F from 1 to 10 g catalyst·h/mol feed stream. In some embodiments, the feed stream is flowed through a column containing the catalyst at a weight hourly space velocity (WHSV) from 0.3 to 12 $h^{-1}$, such as a WHSV from 3 to 8 $h^{-1}$. In certain embodiments, the catalyst is capable of dehydrating at least 5 wt % of the BDO for at least 200 minutes at a temperature of 250-400° C. and a mass hourly space velocity from 3 to 8 $h^{-1}$.

When the product includes MVC, the method may further comprise contacting the product with a solid acid catalyst and dehydrating the MVC to form a subsequent product comprising 1,3BD. Exemplary solid acid catalysts include silicoaluminate, alumina, and sulfated zirconia.

In some embodiments, BDO is converted to 1,3BD by (i) contacting a BDO composition with a first catalyst maintained at a temperature within a range of 250° C. to 700° C., wherein the first catalyst comprises $M_xO_y$ as described above; (ii) dehydrating at least 5 wt % of the BDO with the first catalyst to form a product including MVC, 1,3BD, or a combination thereof; (iii) subsequently contacting the product with a second catalyst comprising a solid acid catalyst maintained at a temperature with a range of 250° C. to 700° C.; and (iv) dehydrating at least 5% of the MVC with the solid acid catalyst to form a subsequent product comprising 1,3BD. In some examples, the first catalyst dehydrates at least 50 wt % of the BDO. The first catalyst may have a MVC selectivity of at least 50%. The BDO composition may be contacted with the first catalyst at a temperature in the range of 250° C. to 400° C. The product may be contacted with the solid acid catalyst at a temperature in the range of 250° C. to 400° C.

In any or all of the above embodiments, each of the first catalyst and the second catalyst may be provided in a catalyst bed. In some embodiments, each of the first catalyst and the second catalyst is disposed in a column. In one embodiment, the first catalyst is disposed in a first column, and the solid acid catalyst is disposed in a second column fluidly connected to the first column. In another embodiment, the first catalyst bed and the second catalyst bed are disposed serially in a single column such that the composition is contacted with the first catalyst and subsequently is contacted with the solid acid catalyst. In yet another embodiment, the first catalyst bed and the second catalyst bed are combined to form a mixed catalyst bed comprising the first catalyst and the solid acid catalyst. In any or all of the above embodiments, the BDO composition and/or the MVC-containing product may be flowed through the column(s) at a flow rate effective to produce a W/F (catalyst weight (g)/feed flow rate (mol/h)) value within a range of 0.5 to 100 g catalyst·h/mol feed stream. In any or all of the above embodiments, the first catalyst may be $In_2O_3$. In any or all of the above embodiments, at least 50% of the BDO may be dehydrated with the first catalyst.

The foregoing and other objects, features, and advantages of the invention will become more apparent from the following detailed description, which proceeds with reference to the accompanying figures.

DETAILED DESCRIPTION

Figure 1:
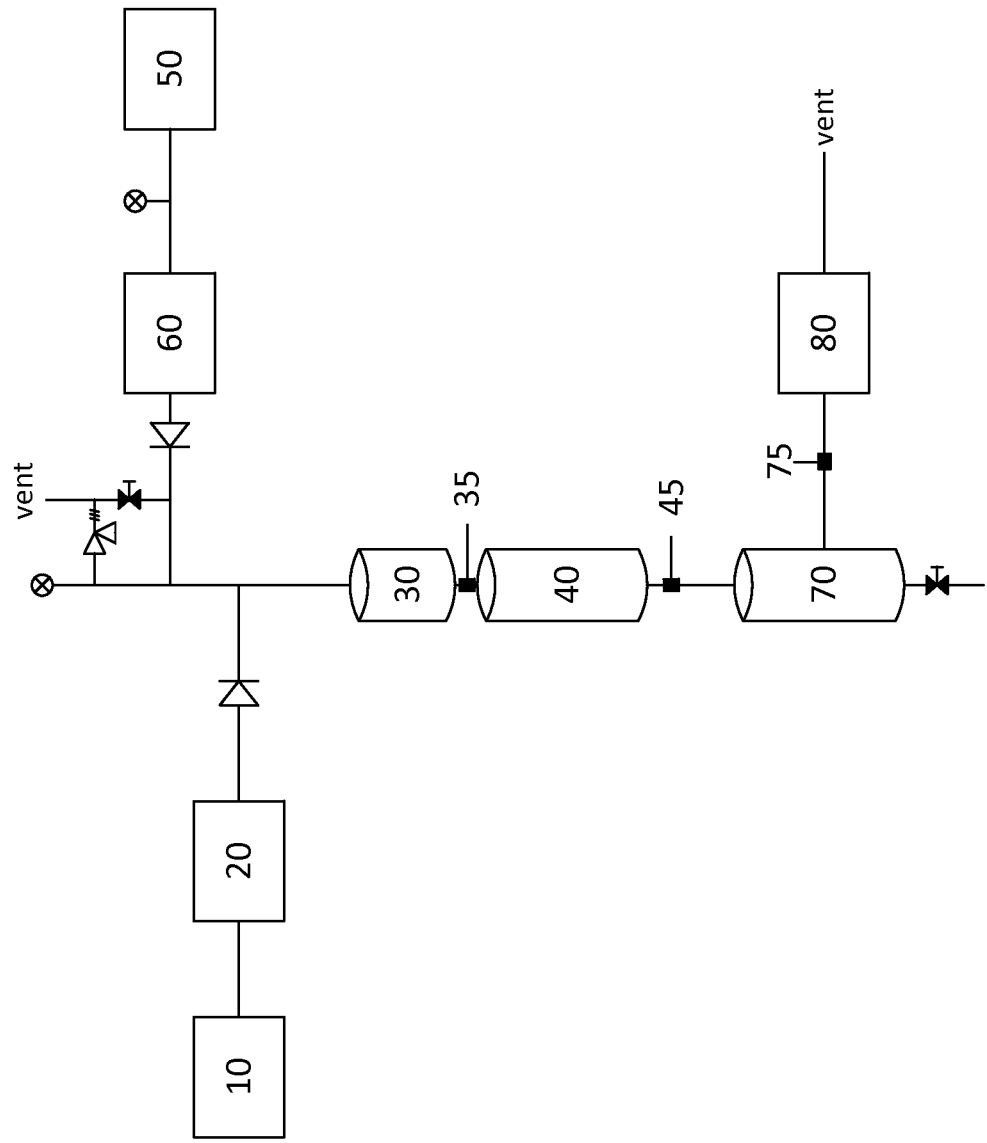
FIG. 1 is a process flow diagram of a continuous, fixed-bed flow reactor, as used in Example 3.

This disclosure concerns embodiments of catalysts and methods for dehydrating 2,3-butanediol to form 1,3-butadiene. As used herein, dehydration refers to a reaction that removes $H_2O$ from an alcohol to form an alkene. A diol, such as 2,3-butanediol may be partially dehydrated by removing one $H_2O$ molecule, or completely dehydrated by removing two $H_2O$ molecules. Thus the term "dehydration" may refer to partial or complete dehydration of 2,3-butanediol. As shown below, BDO is initially dehydrated to methyl vinyl carbinol (MVC). MVC may be further dehydrated to form 1,3BD.

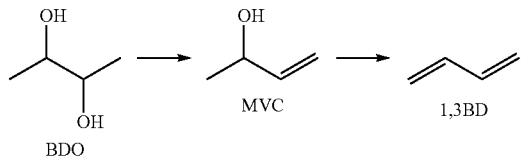

The conventional catalyst for forming 1,3BD is radioactive thoria ($ThO_2$), reported by M. E. Winfield (*J. Coun. Sci. Industr. Res. Aust.,* 18, 412-23, 1945; *Australian Journal of Scientific Research Series a-Physical Sciences* 3(2): 290-305, 1950). In the presence of water formed by the dehydration reaction, however, activity may be retarded and conversion may be incomplete. A common undesirable side product of the reaction is methyl ethyl ketone (MEK). Thus, a need exists for a non-radioactive catalyst and method for making 1,3BD from BDO.

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of ingredients, properties such as molecular weight, percentages, and so forth, as used in the specification or claims are to be understood as being modified by the term "about." Unless otherwise indicated, non-numerical properties, such as anhydrous, as used in the specification or claims are to be understood as being modified by the term "substantially," meaning to a great extent or degree. Accordingly, unless otherwise indicated, implicitly or explicitly, the numerical parameters and/or non-numerical properties set forth are approximations that may depend on the desired properties sought, limits of detection under standard test conditions/methods, limitations of the processing method, and/or the nature of the parameter or property. When directly and explicitly distinguishing embodiments from discussed prior art, the embodiment numbers are not approximates unless the word "about" is recited.

1,3BD: 1,3-butadiene

BDO: 2,3-butanediol

Calcine: As used herein, the term "calcine" means to heat a solid to a temperature below its melting point to bring about a state of thermal decomposition, remove crystalline waters of hydration, change the catalyst or support crystal structure, change the catalyst crystallite size, and/or to oxidize some metals.

Catalyst: A substance that increases the rate of a chemical reaction without itself being consumed or undergoing a chemical change. A catalyst also may enable a reaction to proceed under different conditions (e.g., at a lower temperature) than otherwise possible.

Dopant: As used herein, dopant refers to an element added to a catalyst, to alter the catalyst's properties. A dopant may, for example, alter the acidity, catalytic activity, and/or stability (e.g., the active lifetime) of the catalyst.

MEK: methyl ethyl ketone

MVC: methyl vinyl carbinol, 3-buten-2-ol

Rare earth metal: As defined by IUPAC, rare earth metals include the fifteen lanthanides plus scandium and yttrium. Accordingly, rare earth metals include Sc, Y, La, Ce, Pr, Nd, Pm, Sm, Eu, Gd, Tb, Dy, Ho, Er, Tm, Yb, and Lu.

SCCM: standard cubic centimeters per minute

Selectivity: As used herein, selectivity refers to the ability of a catalyst to direct a reaction to preferentially form a particular product. For example, suppose a catalyst can dehydrate compound A to form compound B, compound C, or a mixture of compounds B and C. If the catalyst has a compound B selectivity of 90%, compound A will be dehydrated to form 90% compound B and 10% compound C. Selectivity may be determined by analysis of the products formed by the reaction. In certain examples herein, selectivity was determined by gas chromatography/mass spectrometry of reaction products.

Solid acid catalyst: A solid catalyst including Brønsted acid (proton donor) and/or Lewis acid (electron-pair acceptor) sites, e.g., catalysts including protons or acidic groups, such as sulfonic acid groups. Solid acid catalysts include, but are not limited to, acidic zeolites (e.g., H-ZSM-5, modenite, Y-zeolite), montmorillonite, kaolinite, aluminas, silicas, aluminosilicates, sulfated zirconia, heteropolyacids, metal oxides, metal salts such as metal sulfides, metal sulfates, metal sulfonates, metal nitrates, metal phosphates, metal phosphonates, metal molybdates, metal tungstates, and certain cation exchange resins (e.g., cation exchange resins that are stable at the operating temperatures).

W/F: A ratio of catalyst weight to feed flow rate:

$$W/F=(\text{grams catalyst} \times \text{hours})/(\text{total moles fed})$$

WHSV: Weight hourly space velocity. WHSV is defined as the mass of BDO flowing per mass of catalyst per hour.

Zeolite: The term "zeolite" refers to any one of a group of crystalline microporous aluminosilicates. Some zeolites include cations (e.g., $H^+$, group IA cations or IIA cations) in the pores. Acidic zeolites include $H^+$ cations. Zeolites are often referred to as molecular sieves since they can be used to selectively sort molecules by size based on size exclusion from the pores. Zeolites may be characterized by pore size and/or by the Si/Al ratio. H-ZSM-5 is an exemplary acidic zeolite having medium-size pores with channels defined by 10-membered rings of alternating silicon (or aluminum) and oxygen atoms. For example, H-ZSM-5 may have a high $Si^{4+}/Al^{3+}$ ratio (e.g., 20-30) with a proton for each $Al^{3+}$ cation to keep the material charge neutral.

II. CATALYSTS

Some embodiments of the disclosed catalysts for converting BDO to MVC and/or 1,3BD have a general formula $M_xO_y$ wherein M is a rare earth metal (i.e., Sc, Y, La, Ce, Pr, Nd, Pm, Sm, Eu, Gd, Tb, Dy, Ho, Er, Tm, Yb, Lu), a group IIIA metal (i.e., In, Ga), zirconium, or a combination thereof, and x and y have values based upon the oxidation state of M. For example, if M has an oxidation state of 3+, x will be 2 and y will be 3, e.g., $In_2O_3$. Similarly, if M has an oxidation state of 4+, x will be 1 and y will be 2, e.g., $ZrO_2$. In some embodiments, the catalyst is not $CeO_2$. In certain embodiments, M is In, Sc, La, Tm, Zr, or a combination thereof. In some instances, the catalysts include waters of hydration, e.g., $Zr(OH)_4$—$Ca(OH)_2$ (or $ZrO_2 \cdot 2H_2O$—$CaO \cdot H_2O$), $Zr(OH)_4$ (or $ZrO_2 \cdot 2H_2O$). In other examples, the catalysts are calcined before use and are substantially anhydrous when first contacted with feed. Catalysts might become more or less hydrated with use.

In certain embodiments, the catalyst further comprises $M^2$, wherein $M^2$ is a rare earth metal, a group IA, IIA or IIIA metal, Zr, or a combination thereof, and wherein $M^2$ is different than M. $M^2$ may be a dopant, such as a dopant present in an amount less than or equal to 20 mol %, ≤15 mol %, ≤10 mol %, or ≤5 mol %. In some instances, $M^2$ may be a basic metal such as a Group IIA metal, e.g., calcium, such as Ca-doped $ZrO_2$. A basic metal may reduce the number of Brønsted acid sites on the catalyst and/or introduce oxygen deficiencies, thereby increasing the catalyst selectivity towards forming MVC and/or 1,3BD rather than MEK. The MVC subsequently is dehydrated to form 1,3BD. $M^2$ also may stabilize the catalyst (such as by reducing degradation) and/or increase its reactivity, thereby increasing the catalyst lifetime and/or increasing the yield of MVC and/or 1,3BD.

Metal phosphate catalysts also may be suitable for converting BDO to MVC and/or 1,3BD. In some embodiments, the metal phosphate catalysts have a general formula $M^3_a(PO_4)_b$ where $M^3$ is a group IA, a group IIA metal, a group IIIA metal, or a combination thereof, and a and b have values based upon the oxidation state of $M^3$. For example, when $M^3$ has an oxidation state of 2+, a is 3 and b is 2, e.g., $Mg_3(PO_4)_2$. In some embodiments, $M^3$ is Ba, Li, Ca, Mg, B, or a combination thereof. Exemplary phosphate catalysts include $Ba_3(PO4)_2$, $LiCaPO_4$, $BPO_4$, and $Mg_3(PO4)_2$. In certain embodiments, a metal phosphate catalyst further comprises a dopant $M^2$, where $M^2$ is as described above.

In some embodiments, the catalyst is (i) an oxide of In, Al, La, and Zr, (ii) an oxide of Al and Zr, (iii) an oxide of Zr and Ca, (iv) $Tm_2O_3$, (v) $ZrO_2$, (vi) $Sc_2O_3$ or (vii) $In_2O_3$. In certain examples, the catalyst is $In_2O_3$.

The catalyst may be disposed on a support, such as a non-acidic support (i.e., a support that has a relatively fewer number Brønsted and/or Lewis acid sites compared to Brønsted and/or Lewis base sites). Suitable non-acidic supports include low-alumina silicas and carbons. The support may itself be a catalyst, such as zirconia. For example, $Tm_2O_3$ may be disposed on a zirconia support. In addition, the catalyst may be disposed on the support such that the support never contacts the feed (i.e., an "egg-shell" type catalyst that substantially completely covers the support), allowing broader selection of useful support materials.

Catalyst reactivity may be affected by particle size and/or surface area. In some instances, increasing a catalyst's surface area increases the catalyst's reactivity and the 1,3BD and/or MVC yield. Thus, the catalyst may be comminuted to reduce its particle size and increase its surface area. In some embodiments, the catalyst has an average particle size less than 0.5 mm, such as an average particle size from 0.05 mm to 0.5 mm, 0.1 mm to 0.5 mm, or 0.1 mm to 0.25 mm. The catalyst may have a surface area of at least 50 $m^2/g$ or at least 100 $m^2/g$, such as a surface area from 50 $m^2/g$ to 1000 $m^2/g$, from 100 $m^2/g$ to 750 $m^2/g$, from 100 $m^2/g$ to 600 $m^2/g$, or from 300 $m^2/g$ to 600 $m^2/g$.

Embodiments of the disclosed catalysts have an MVC and/or 1,3BD selectivity of at least 20%, such as at least 30%, at least 40%, at least 50%, at least 60%, or at least 70%.

III. CATALYST SYNTHESIS

Some embodiments of the disclosed metal oxide catalysts are prepared by thermal decomposition of their hydrated nitrate or oxalate salts. A hydrated nitrate salt is heated at or above its decomposition temperature for a period of time effective to produce a metal oxide. In certain examples, catalysts were prepared by thermal decomposition of their hydrated nitrate salts at temperatures ranging from 450° C. to 850° C.; typically, the nitrate salt was heated for 2 hours. In some embodiments, a metal oxide catalyst is prepared by forming a metal oxalate precursor and then thermally decomposing the metal oxalate to produce metal oxide.

Other metal oxide catalysts can be prepared by depositing a metal oxide onto a support. In some examples, a metal nitrate was combined with hydrous zirconia (denoted as $Zr(OH)_4$, $ZrO(OH)_2$, or $ZrO_2 \cdot 2H_2O$) and ammonia was added to precipitate the metal onto the zirconia. The solids were dried to form a metal oxide on dried $Zr(OH)_4$. In other examples, a metal nitrate was combined with calcined zirconia ($ZrO_2$), and ammonia was added to precipitate the metal. The solids were calcined to form a metal oxide on calcined zirconia.

Doped metal oxide catalysts can be made by combining nitrate salts in desired amounts and forming metal oxides by any of the above methods. In one example, a calcium-doped $Lu_2O_3$ catalyst was formed by combining lutetium and calcium nitrate salts with oxalic acid to form an oxalate precursor, which was dried and calcined at 550° C. for 6 hours to produce the calcium-doped $Lu_2O_3$ catalyst.

In one embodiment, a $HfO_2$ catalyst was prepared by precipitating the hydrous oxide from a solution of hafnium chloride using aqueous ammonia, and then drying and calcining the solid at 600° C. In another embodiment, a $ZnO/SiO_2$ catalyst was prepared by mixing a zinc nitrate solution with a silica sol, drying the mixture, and calcining the resulting solids at 600° C. for 2 hours. In still another embodiment, a mixed oxide of aluminum and zinc was prepared by a co-precipitation procedure. A first solution containing dissolved ammonium carbonate was added to a second solution containing dissolved aluminum nitrate and zinc nitrate. The resulting precipitate was washed, then dried and calcined at 600° C. for 2 hours.

Embodiments of the disclosed phosphate catalysts can be prepared by dissolving a metal salt in water, and then adding the solution dropwise to a solution of aqueous ammonium phosphate. The precipitated metal phosphate is washed, dried (e.g., under vacuum), and ground to produce a powder.

IV. METHODS FOR CONVERTING BDO TO MVC AND/OR 1,3BD

Embodiments of the disclosed catalysts are capable of dehydrating BDO to form MVC and/or 1,3BD. A feed stream including BDO is contacted with the catalyst. The feed stream may comprise at least 5 wt % BDO, such as from 5 wt % to 100 wt % BDO. In some embodiments, the feed stream is an aqueous composition comprising BDO. BDO may be obtained from any source. For example, BDO may be obtained as a byproduct of CO fermentation, a byproduct of anaerobic microbial saccharide (e.g., glucose, lactose, galactose) fermentation, or by any other fermentive or thermal process. All isomers of BDO may be used, i.e., d-, l-, and meso isomers.

BDO is exposed to the catalyst by bringing the feed stream comprising BDO, in liquid or gas phase, into contact with the catalyst for an effective period of time at an effective temperature and pressure for dehydration to occur as discussed below. BDO may be contacted with the catalyst by any suitable means, including combining BDO and the catalyst in a closed vessel, or flowing BDO across and/or through a catalyst bed, such as a catalyst bed disposed in a column.

At least 3% of the BDO is dehydrated by the catalyst to form a product comprising MVC, 1,3BD, or a mixture thereof. By "at least 3%" is meant at least 3% of an initial mass or concentration of BDO in the feed stream prior to contact with the catalyst. A person of ordinary skill in the art understands that a percentage of the initial mass or concentration may be a weight percent, a mole percent, or even a volume percent. For example, if the feed stream comprises 10 wt % BDO, at least 3% dehydration forms a product comprising no more than 9.7 wt % BDO. In some embodiments, the catalyst is capable of dehydrating at least 5%, at least 10%, at least 30%, at least 50%, at least 70%, at least 75%, at least 90%, or even at least 95% of the BDO to form a product comprising MVC and/or 1,3BD. When the product comprises MVC, the product may be contacted with a subsequent catalyst to further dehydrate the MVC and form 1,3BD.

The feed stream may be contacted with the catalyst at a temperature within a range of 250-700° C., 250-500° C., 250-400° C., 300-450° C., or 300-350° C. The feed stream may be contacted with the catalyst at a pressure within a range of 50 mm (6.7 kPa) to 50 atmospheres (5.1 MPa). In some embodiments, the feed stream is contacted with the catalyst at atmospheric pressure. In other embodiments, the feed stream is contacted with the catalyst at a pressure less than atmospheric pressure, such as a pressure within a range of 50 mm (6.7 kPa) to 750 mm (100 kPa). Reduced pressure may reduce contact time, e.g., by facilitating removal of products from the catalyst surface. In some embodiments, reducing contact time facilitates conversion to MVC and/or 1,3BD without formation of undesirable byproducts, e.g., condensation products. In other embodiments, the feed stream is contacted with the catalyst at a pressure higher than atmospheric, such as a pressure within a range of 1 atm (0.1 MPa) to 50 atm (5.1 MPa).

In some embodiments, dehydration is a continuous or substantially continuous process in which a BDO feed stream flows across or through a catalyst bed. For example, a column containing a packed catalyst bed is prepared, and a BDO feed stream is flowed through the column. The catalyst in the column is heated to an effective temperature, e.g., with a range of 250° C. to 700° C. In some embodiments, a partial vacuum is applied to the column so that the column operates at a pressure less than atmospheric pressure. In other embodiments, the column is operated at ambient, or atmospheric, pressure. In still other embodiments, the column is operated at a pressure greater than atmospheric pressure.

In some embodiments, the BDO feed stream is introduced into the column at ambient temperature. Alternatively, the BDO feed stream may be preheated to a desired reaction temperature before flowing into the column.

A person of ordinary skill in the art will appreciate that BDO feed stream flow rates through the column are affected by a number of variables including, but not limited to, catalyst composition, column dimensions, temperature, pressure, BDO concentration, and combinations thereof. The BDO feed stream may have a weight hourly space velocity (WHSV) within a range of 0.3 to 12 $h^{-1}$, such as 0.5 to 12 $h^{-1}$, 1 to 10 $h^{-1}$, 2 to 9 $h^{-1}$, 3 to 8 $h^{-1}$, 4 to 7 $h^{-1}$, or 5 to 6 $h^{-1}$. In some examples, the WHSV was within a range of 5 to 6 $h^{-1}$.

A carrier gas may flow concurrently through the column with the BDO feed stream. Suitable gases include inert gases (e.g., nitrogen, helium, argon), hydrogen, air, and combinations thereof. In some examples, the gas was nitrogen or helium. The carrier gas flow rate is affected by a number of variables including, but not limited to catalyst composition, column dimensions, temperature, pressure, BDO concentration, and combinations thereof.

The carrier gas flow rate and/or BDO feed stream flow rate are selected to achieve a desired contact time. In some embodiments, flow rates are chosen to attain W/F (catalyst weight/feed flow rate) values in a range of 0.5 to 100 g catalyst·h/mol feed stream, such as from 0.5 to 50, from 1 to 25, or from 1 to 10 g catalyst·h/mol feed stream.

In some embodiments, the column is purged with the carrier gas before the BDO feed stream is introduced into the column. The column may be heated during the carrier gas purge to regenerate the catalyst, e.g., by removing adsorbed water and/or by-products (e.g., oligomeric condensation products) adsorbed during prior use.

A chilled receiver vessel may be fluidly connected to a distal end of the column so that product exiting the column is chilled and condensed to a liquid. Alternatively, products may be collected by adsorption onto a suitable adsorbent (e.g., a Carbopack™ (graphitized carbon) bed) or trapping in a solvent (e.g., diglyme) at a reduced temperature (e.g., less than 50° C.), and subsequently released by heating the adsorbent or solvent.

Some embodiments of the disclosed catalysts, when contacted with a BDO feed stream, remain capable of dehydrating at least 5% of the BDO in the feed stream for at least 200 minutes, at least 300 minutes, or at least 500 minutes at a temperature of 250-400° C. and a WHSV of 3-8 $h^{-1}$. In certain embodiments, the disclosed catalyst when contacted with a BDO feed stream remains capable of dehydrating at least 5% of the BDO in the feed stream for at least 500 minutes at a temperature of 250-350° C. and a WHSV of 5 to 6 $h^{-1}$.

In some embodiments, the primary product is methyl vinyl carbinol. For example, $In_2O_3$ is a catalyst that selectively converts BDO to MVC. In some examples, $In_2O_3$ converts BDO to MVC with an MVC product selectivity of at least 50%, at least 60%, or at least 70%.

A product comprising MVC (MVC composition) may be contacted with a subsequent catalyst that is capable of further dehydrating MVC to form 1,3BD. Suitable catalysts for dehydrating MVC include solid acid catalysts including, but not limited to, aluminosilicates (e.g., zeolites), alumina, and sulfated zirconia. The MVC composition may be contacted with the solid acid catalyst at a temperature within a range of 250-700° C., 250-500° C., 250-400° C., 300-450° C., or 300-350° C. The MVC composition may be contacted with the solid acid catalyst at a pressure within a range of 50 mm (6.7 kPa) to 50 atmospheres (5.1 MPa). In some embodiments, the MVC composition is contacted with the catalyst at atmospheric pressure. In other embodiments, the MVC composition is contacted with the catalyst at a pressure less than atmospheric pressure, such as a pressure within a range of 50 mm (6.7 kPa) to 750 mm (100 kPa). In some embodiments, the catalyst dehydrates at least 5% of the methyl vinyl carbinol (i.e., at least 5% of an initial mass or concentration of MVC present in the MVC composition prior to contact with the catalyst) to form a second product comprising 1,3-butadiene.

Dehydration with a solid acid catalyst may be a continuous or substantially continuous process in which a composition comprising MVC flows across or through a catalyst bed. For example, a column containing a packed catalyst bed is prepared, and a composition comprising MVC is flowed through the column. The MVC composition may be introduced into the column at ambient temperature, or the MVC composition may be preheated before flowing into the column. A carrier gas may flow concurrently through the column with the MVC composition.

In some embodiments, the solid acid catalyst is disposed in a second column downstream from a first column that includes a first catalyst capable of dehydrating BDO to form a product comprising MVC. The first and second columns may be operated under the same or different conditions (e.g., temperature, WHSV, W/F, carrier gas, pressure, etc.) In one embodiment, the columns are in fluid communication such that a first product comprising MVC exits via an outlet of the first column and flows directly into the second column via an inlet of the second column.

In another embodiment, the first catalyst and the solid acid catalyst are disposed within a single column such that, for example, a first zone within the column contains the first catalyst bed and a second, downstream zone within the column contains the solid acid catalyst bed. The zones may be at the same or different temperatures. In still another embodiment, the first catalyst and the solid acid catalyst are mixed to form a mixed catalyst bed within a single column.

V. EXAMPLES

Materials

Methyl ethyl ketone (99+%) and 2,3-butanediol were obtained from Aldrich Chemical Co. The Aldrich BDO (98%) was a mixture of meso- (~76%) and racemic d/l isomers (~24%). BDO obtained from LanzaTech was a d/l mixture (~95%) and contained very little meso isomer (~3%).

Pyroprobe GC/MS Apparatus

The pyroprobe unit used in this work was a CDS Analytical, Inc. Series 5000 pyroprobe (model 5200). The pyroprobe was equipped with an optionally used downstream heated catalyst bed, and a heated Carbopack adsorbent bed located between the catalyst bed and the gas chromatograph (GC) inlet. The GC used was an Agilent Technologies 7890A GC system, equipped with an Agilent Technologies 5975C inert XL mass spectroscopic (MS) detector with Triple-Axis Detector. The GC column used for product separation was a DB5 column.

Catalyst Preparations

Several classes of catalysts for the conversion of 2,3-butanediol to butadiene were prepared for high-throughput screening. Representative examples of the preparations of these catalysts are described here. Other catalysts used in screening experiments were purchased or obtained as free samples from commercial vendors.

Oxide by Nitrate Decomposition

Metal oxide catalysts were prepared by thermal decomposition of their nitrate salts. The respective metal nitrate decomposition temperatures (Table 1) were found in the literature (Wendlandt, *Analytica Chimica Acta,* 15:435-439, 1956; Wendlandt, *J. of Inorg. and Nuclear Chem.,* 12(3,4): 276-280, 1960; Haire, R. G. "The Thermal Decomposition of Berkellium Compounds", Link: http://www.osti.gov/bridge/purl.cover.jsp?purl=/44549027-yMjUrq/). The preparations of La and Nd oxides are described and are illustrative of the method used. The decomposition temperatures of $La(NO_3)_3.6$ $H_2O$ and $Nd(NO_3)_3.6$ $H_2O$ were reported to be 780° C. and 830° C., respectively. Two grams of each of the above salts were placed in porcelain crucibles and place in a muffle furnace. A low flow of air was admitted. Crucibles were heated to 850° C. at 5° C./min, held for 2 h, and cooled to ambient at 10° C./min. The resulting oxides were ground to a fine powder (catalysts 5-6 and 5-7 in Example 2).

Metal nitrates were precursors for metal oxides deposited on various supports. $In_2O_3$ was supported on silica gel by impregnating indium nitrate into Sigma Aldrich Grade 7754 Silica Gel (70-230 mesh). The appropriate weight of indium nitrate to make a 10% $In_2O_3$ loaded silica was dissolved in the previously determined impregnation volume. The indium solution was added dropwise to the silica with vigorous mixing to make a free-flowing powder. The powder was dried slowly in an oven with periodic shaking to encourage uniform drying. The material was then calcined in air at 500° C. (5° C./min heating rate) and held for 2 hours. The cooled catalyst was light yellow.

10 wt % $In_2O_3$ on Hyperion CS-02C-063-XD was prepared by impregnation with an aqueous indium nitrate solution. The impregnated material was tumbled to age the catalyst precursor, dried during tumbling under a stream of hot air to remove most of the water, then further dried in a vacuum oven at 75° C. The dried material was then washed with 28% ammonia to convert the indium to the insoluble hydroxide form. The material was then dried in the vacuum oven at 75° C., then at atmospheric pressure at 115° C. This material was used for catalyst testing.

TABLE 1

Nitrate decomposition temperatures in rare-earth oxide synthese

| Rare-earth Oxide | Nitrate Decomposition Temperature (° C.) |
|---|---|
| $La_2O_3$ | 850° C. |
| $Pr_6O_{11}$ | 550° C. |
| $Nd_2O_3$ | 850° C. |
| $Sm_2O_3$ | 750° C. |
| $Eu_2O_3$ | 800° C. |
| $Gd_2O_3$ | 800° C. |
| $Tb_4O_7$ | 450° C. |
| $Dy_2O_3$ | 800° C. |
| $Ho_2O_3$ | 650° C. |
| $Er_2O_3$ | 650° C. |
| $Tm_2O_3$ | 650° C. |
| $Yb_2O_3$ | 750° C. |
| $Lu_2O_3$ | 600° C. |
| $Y_2O_3$ | 500° C. |
| $Sc_2O_3$ | 550° C. |

Oxide by Oxalate Decomposition

Metal oxide catalysts were prepared from their oxalate precursors, which in turn were prepared from the nitrates by precipitation with oxalic acid. The preparation of $In_2O_3$ is illustrative. 14.08 g $In(NO_3)_3.5 H_2O$ was dissolved in 50 mL $H_2O$. 6.81 g oxalic acid was dissolved in 30 mL $H_2O$ with gentle heating. Addition of the oxalic acid to the indium nitrate solution resulted in the formation of a thick white gel, which was filtered and washed three times. The resulting solid was dried at 120° C. for 2 h, then heated to 550° C. at 5° C./min, held for 4 h, then cooled to 30° C. at about 10° C./min. The solid was ground to a fine powder and recalcined at 550° C. for 2 h to give a dull yellow powder (catalyst 4-4 in Example 2).

Similarly, $In_2O_3$ can be prepared using ammonium oxalate in place of oxalic acid. 16.90 g $In(NO_3)_3.5 H_2O$ was dissolved in 50 mL $H_2O$. 9.21 g ammonium oxalate was dissolved in 85 mL $H_2O$ with gentle heating. Addition of the ammonium oxalate to the indium nitrate solution resulted in the formation of a thick white precipitate. The volume of the mixture was reduced by gentle evaporation and the remaining slurry was placed into an oven at 90° C. to dry overnight. The resulting solid was then heated to 550° C. at 2° C./min, held for 6 h, then cooled to 25° C. at about 3° C./min. The fluffy yellow solid was pelletized and sieved to a 60-100 mesh fraction for catalyst testing (Table 37 in Example 5).

A portion of the $In_2O_3$ prepared by the ammonium oxalate preparation was doped with lithium ion. Sufficient lithium nitrate was dissolved in water and slurried with a fraction of the $In_2O_3$. The slurry was then slowly dried in an oven at 90° C., then heated to 600° C. at 3° C./h, and held for 4 h to calcine the material. The 60-100 mesh fraction was used for catalyst testing.

$Ga_2O_3$ was prepared from the nitrate by precipitation with ammonium oxalate, in the same manner as described above for $In_2O_3$. The 60-100 mesh fraction was used for catalyst testing.

Oxide Deposited on Dried Hydrous Zirconia ($Zr(OH)_4$)

The preparation of 10% $Sc_2O_3$ on hydrous zirconia is illustrative of this class of catalysts. 10.00 g of water was added to 4.00 g of MEL FZO1501/09 powder (MEL Chemicals) in a beaker. 1.8062 g $Sc(NO_3)_3.5 H_2O$ was dissolved in 10.00 mL $H_2O$ and added to the zirconia slurry with stirring. After about 5 min, 5 mL 29% ammonia solution was added, resulting in coagulation to a gelatinous mass. The solids were filtered and washed several times with $H_2O$, then dried at 60° C. overnight. This uncalcined material was used as a catalyst in screening experiments (catalyst 2-3 in Example 2). In addition, a portion of the material was calcined at 550° C. for 2 h and also screened for catalytic activity (catalyst 2-4 in Example 2).

Oxide Deposited on Calcined $Zr(OH)_4$

Hydrous zirconia powder (MEL FZO1501/06) was heated to 550° C. at 5° C./min, calcined at 550° C. for 4 h, then cooled to ambient. As a representative example of the general preparation used, 6.98 g of this material was slurried with 100 mL $H_2O$. $Tm(NO_3)_3.5 H_2O$ (1.79 g) was dissolved in $H_2O$ (30 mL) and added to the zirconia slurry with stirring. 29% ammonia solution (10 mL) was then added to form a gel, which was filtered and washed several times. The filter cake was dried under house vacuum at 80° C. overnight, then calcined with a flow of air at 550° C. for 2 h (catalyst 1-6 in Example 2).

Calcium-Doped Oxide Via Oxalate Decomposition

As one example, 11.79 g $Lu(NO_3)_3.x H_2O$ and 0.40 g $Ca(NO_3)_2.4 H_2O$ were dissolved in 100 mL $H_2O$. 4.97 g of oxalic acid was dissolved in 50 mL warm $H_2O$ and added to the Lu/Ca solution to form a gel. Solids were filtered and washed several times with $H_2O$ and dried at 80° C. under house vacuum overnight. The solid product was then calcined at 550° C. for 6 h in flowing air (catalyst 4-6 in Example 2).

Other Oxide Preparations

Hafnium oxide, $HfO_2$, was prepared by precipitating the hydrous oxide from a solution of hafnium chloride using an aqueous ammonia solution. The precipitate was washed, dried, and calcined at 600° C. prior to use.

A 50% ZnO/50% $SiO_2$ catalyst was prepared by mixing a zinc nitrate solution with a silica sol, drying the mixture, and calcining the resulting solids at 600° C. for 2 hours.

An $Al_{0.75}Zn_{0.25}O_x$ catalyst composition was prepared that had previously been reported (Bhattacharyya, *Ind. Eng. Chem. Process Des. Dev.*, 2(1), 45-51, 1963). The method used to prepare the catalyst was a co-precipitation procedure. A first solution containing dissolved ammonium carbonate was added to a second solution containing dissolved aluminum nitrate and zinc nitrate. The resulting precipitate was deionized water washed, then dried and calcined at 600° C. for 2 hours.

Phosphate Catalyst Preparation

Phosphate catalysts were synthesized by a method typified by the synthesis of barium phosphate described here. 10.19 g of diammonium hydrogen phosphate $[(NH_4)_2HPO_4]$, 29 mL of 29% aqueous ammonia $[NH_3]$, and 100 mL of deionized (DI) water were combined. The contents were gently heated and stirred to completely dissolve the solids. 28.97 g of barium acetate $[Ba(C_2H_3O_2)_2]$ and 10 mL of DI water were added together and mixed well at room temperature for several minutes until the solids were dissolved. The $Ba(C_2H_3O_2)_2$ solution was added drop wise to the $(NH_4)_2HPO_4$ solution while stirring continuously. After all the solution was added, stirring was ceased and the fine-grain white precipitate that formed was settled out. After allowing the solids to settle for ~20 minutes, the supernatant solution (nearly water white) was drawn off without disturbing the settled solids. Then, 200 mL of fresh DI water was added to the beaker to wash the solids and stirred vigorously for a few minutes. The re-slurried solids were allowed to settle for ~20 minutes and the clear solution above the settled solids was drawn off. The washing procedure was repeated one more time. Then, the twice-washed slurry was vacuum filtered using a Millipore® 0.45 μm filter. The filter cake was additionally washed on the filter with ~250 mL of fresh DI water. After washing, the filter cake was allowed to air dry on the filter for ~1 hour, and then the filter assembly and the cake were placed in a vacuum oven overnight at 120° C. The dried cake was removed from the vacuum oven and recovered from the filter. The soft powder chunks were ground gently in a mortar and pestle for uniformity (catalyst 4-13 in Example 2).

Commercial Catalysts

Commercial catalysts were obtained from MEL Chemicals, Degussa (Evonik), Praxair, Coorstech, Alfa-Aesar, Engelhard, Tosoh, Unitec Ceramics, Teledyne Wah Chang, and Cerac as indicated in Table 3.

Example 1

Pyroprobe Evaluation of Catalysts

The feedstock was 10 wt % BDO (Aldrich) in deionized (DI) water. The catalyst (~2 mg of powder) was loaded into a quartz tube (25 mm long×1.9 mm I.D.; open at both ends), and held in position using a quartz wool plug on both ends of the powder layer. Approximately 1 μL of feed solution was subsequently dispensed onto the back quartz wool plug then loaded into the pyroprobe wand with the liquid-containing end down, so that upon heating the liquid feed vapors would be carried through the catalyst bed. After the tube was loaded into the pyroprobe wand, the end of the wand was inserted into the pyroprobe unit and sealed. Helium carrier gas flowed through the probe wand and over the quartz wool plugs and catalyst. Upon initiation of the unit, a heating coil encircling the quartz tube, rapidly heated the tube and its contents to ~600° C. and maintained it at that temperature for usually 15 seconds. Carrier gas flows were typically 20 cc/m of He through the pyroprobe. Reactant and product vapors were rapidly carried out of the quartz tube and adsorbed onto a Carbopack bed at 40° C., then later desorbed from the adsorbent bed at 300° C. The desorbed products were carried into the GC/MS unit for separation and analysis. Area percent reports were generated for percent conversion of BDO and product selectivity to 1,3 butadiene, methyl vinyl carbinol, MEK, and isobutyraldehyde (IBA). Aldrich BDO was a mixture of d/l and meso isomers. Early analyses integrated over both isomers (reported as BDO) until method improvements allowed separate quantification.

Conversion and product selectivity data were based on GC/MS area percents for BDO feedstock and other products produced. A ranking of the nine best pyroprobe test results are shown in Table 2. A complete listing of results obtained from all of the catalysts tested is presented in Table 3. Catalysts that produced 1,3BD and/or MVC were considered, since MVC is relatively easily converted to 1,3BD. The catalyst designation, the optimum test temperature used, and the combined 1,3BD+MVC yield for that condition are given for each of the nine best catalyst/conditions tested. Optimal temperatures in the pyroprobe are not necessarily the optimal temperatures in other reactor designs.

TABLE 2

Best results for 1,3BD and MVC production in pyroprobe testing

| Catalyst | Optimal T, ° C. | 1,3BD + MVC % Yield |
|---|---|---|
| MEL ALZ22[1] | 500 | 61.4 |
| MEL XZO691-01[2] | 500 | 58.0 |
| $Tm_2O_3$[3] | 500 | 56.3 |
| MEL ALZ22[1] | 500 | 56.0 |
| MEL FZO2089[3] | 500 | 53.8 |
| MEL ALZ5C-4/D[4] | 500 | 48.7 |
| MEL ALZ22[1] | 500 | 42.7 |
| MEL FZO922[5] | 500 | 33.9 |
| $Sc_2O_3$ | 700 | 31.7 |

[1] A mixed oxide of Al, La, and Zr, obtained from MEL Chemicals, Inc.
[2] $Zr(OH)_4$—$Ca(OH)_2$, obtained from MEL Chemicals, Inc.
[3] A mixed oxide of Al, La, and Zr (equivalent to ALZ22), obtained from MEL Chemicals, Inc.
[4] A mixed oxide of Al and Zr, obtained from MEL Chemicals
[5] $Zr(OH)_4$ (or $ZrO_2 \cdot 2H_2O$), obtained from MEL Chemicals As shown in Table 2, mixed oxides including Al, La, and Zr performed well. Oxides of Al/Zr, Zr/Ca, Tm, and Sc also gave good results.

TABLE 3

Summary of pyroprobe runs for the conversion of BDO to 1,3BD

| Run | Catalyst | Descriptor | Notes | T (° C.) | BDO % Conv. | 1,3BD % Sel. | 1,3BD % Yield | MVC % Sel. | MVC % Yield | MEK % Sel. | MEK % Yield | Other % Sel. | Other % Yield |
|---|---|---|---|---|---|---|---|---|---|---|---|---|---|
| 1 | Silica Gel | Degussa Aerosil 380 | | 300 | 10.0 | 0 | 0 | 0 | 0 | 0 | 0 | 100.0 | 10.0 |
| 2 | Silica Gel | Degussa Aerosil 380 | | 500 | 93.0 | 8.6 | 8.0 | 0 | 0 | 91.4 | 85.0 | 0 | 0 |
| 3 | Alpha Alumina | Coorstech 2886-50-1 | | 300 | 10.0 | 0 | 0 | 0 | 0 | 0 | 0 | 100.0 | 10.0 |
| 4 | Alpha Alumina | Coorstech 2886-50-1 | | 500 | 95.0 | 8.4 | 8.0 | 0 | 0 | 91.6 | 87.0 | 0 | 0 |
| 5 | Pr-doped $CeO_x$ (deoxygenated) | | | 300 | 5.0 | 0 | 0 | 0 | 0 | 0 | 0 | 100.0 | 5.0 |
| 6 | Pr-doped $CeO_x$ (deoxygenated) | | | 500 | 5.0 | 0 | 0 | 0 | 0 | 0 | 0 | 100.0 | 5.0 |
| 7 | Pr-doped $CeO_x$ (deoxygenated) | | | 700 | 5.0 | 0 | 0 | 0 | 0 | 0 | 0 | 100.0 | 5.0 |
| 8 | $CeO_2$ | Alfa-Aesar | 99.9% | 300 | 5.0 | 0 | 0 | 0 | 0 | 0 | 0 | 100.0 | 5.0 |
| 9 | $CeO_2$ | Alfa-Aesar | 99.9% | 500 | 50.0 | 0 | 0 | 0 | 0 | 80.0 | 40.0 | 20.0 | 10.0 |
| 10 | $WO_{2.97}$ | Alfa-Aesar | 99.99% | 300 | 65.0 | 0 | 0 | 0 | 0 | 76.9 | 50.0 | 23.1 | 15.0 |
| 11 | $WO_{2.97}$ | Alfa-Aesar | 99.99% | 500 | 5.0 | 0 | 0 | 0 | 0 | 0 | 0 | 100.0 | 5.0 |
| 12 | $La_2O_3$ | Alfa-Aesar | 99.99% | 300 | 5.0 | 0 | 0 | 0 | 0 | 0 | 0 | 100.0 | 5.0 |

TABLE 3-continued

Summary of pyroprobe runs for the conversion of BDO to 1,3BD

| Run | Catalyst | Descriptor | Notes | T (° C.) | BDO % Conv. | 1,3BD % Sel. | 1,3BD % Yield | MVC % Sel. | MVC % Yield | MEK % Sel. | MEK % Yield | Other % Sel. | Other % Yield |
|---|---|---|---|---|---|---|---|---|---|---|---|---|---|
| 13 | La$_2$O$_3$ | Alfa-Aesar | 99.99% | 500 | 5.0 | 0 | 0 | 0 | 0 | 0 | 0 | 100.0 | 5.0 |
| 14 | 3 mole % Y-Stab. ZrO$_2$ | Degussa VP 3-YSZ (40) | | 300 | 5.0 | 0 | 0 | 0 | 0 | 0 | 0 | 100.0 | 5.0 |
| 15 | 3 mole % Y-Stab. ZrO$_2$ | Degussa VP 3-YSZ (40) | | 500 | 75.5 | 23.3 | 17.6 | 16.7 | 12.6 | 60.1 | 45.4 | −0.1 | −0.1 |
| 16 | La + Al Doped ZrO$_2$ | MEL ALZ22 | | 300 | 10.0 | 0 | 0 | 0 | 0 | 0 | 0 | 100.0 | 10.0 |
| 17 | La + Al Doped ZrO$_2$ | MEL ALZ22 | | 500 | 99.4 | 43.0 | 42.7 | 0 | 0 | 45.8 | 45.5 | 11.3 | 11.2 |
| 18 | La + Al Doped ZrO$_2$ | MEL ALZ22 | (1st Repeat) | 500 | 90.0 | 0 | 0 | 0 | 0 | 100.0 | 90.0 | 0 | 0 |
| 19 | La + Al Doped ZrO$_2$ | MEL ALZ22 | (2nd Repeat) | 500 | 90.0 | 16.4 | 14.8 | 0 | 0 | 66.7 | 60.0 | 16.9 | 15.2 |
| 20 | Quartz Wool | | | | 79.0 | 9.2 | 7.3 | 0 | 0 | 62.2 | 49.1 | 28.6 | 22.6 |
| 21 | La + Al Doped ZrO$_2$ | MEL ALZ22 | (Fresh Cat.) | 500 | 75.0 | 33.3 | 25.0 | 0 | 0 | 48.7 | 36.5 | 18.0 | 13.5 |
| 22 | La + Al Doped ZrO$_2$ | MEL ALZ22 | (1st Repeat) | 500 | 93.5 | 65.7 | 61.4 | 0 | 0 | 26.5 | 24.8 | 7.8 | 7.3 |
| 23 | La + Al Doped ZrO$_2$ | MEL ALZ22 | (2nd Repeat) | 500 | 94.0 | 56.5 | 53.1 | 0 | 0 | 27.8 | 26.1 | 15.7 | 14.8 |
| 24 | La + Al Doped ZrO$_2$ | MEL ALZ22 | (3rd Repeat) | 500 | 50.0 | 41.0 | 20.5 | 0 | 0 | 46.2 | 23.1 | 12.8 | 6.4 |
| 25 | La + Al Doped ZrO$_2$ | MEL ALZ22 | (4th Repeat) | 500 | 92.0 | 50.4 | 46.4 | 0 | 0 | 37.3 | 34.3 | 12.3 | 11.3 |
| 26 | La + Al Doped ZrO$_2$ | MEL ALZ22 | (5th Repeat; N$_2$ flow 60% of that in Run 25) | 500 | 93.3 | 63.2 | 59.0 | 0 | 0 | 30.0 | 28.0 | 6.8 | 6.3 |
| 27 | La + Al Doped ZrO$_2$ | MEL ALZ22 | (6th Repeat; N$_2$ flow 40% of that in Run 25) | 500 | 53.0 | 64.9 | 34.4 | 0 | 0 | 65.1 | 34.5 | −30.0 | −15.9 |
| 28 | 3 mole % Y-Stab. ZrO$_2$ | Degussa VP 3-YSZ (40) | | 500 | 38.0 | 21.1 | 8.0 | 10.8 | 4.1 | 41.6 | 15.8 | 26.6 | 10.1 |
| 29 | 3 mole % Y-Stab. ZrO$_2$ | Degussa VP 3-YSZ (40) | | 500 | 38.0 | 23.7 | 9.0 | 14.5 | 5.5 | 42.9 | 16.3 | 18.9 | 7.2 |
| 30 | 5% Phosphomolybdic acid (PMA) on TiO$_2$ 0720 | Engelhard | | 250 | 53.0 | 0 | 0 | 0 | 0 | 64.2 | 34.0 | 35.8 | 19.0 |
| 31 | 5% PMA on TiO$_2$ 0720 | Engelhard | | 350 | 50.0 | 0 | 0 | 0 | 0 | 58.0 | 29.0 | 42.0 | 21.0 |
| 32 | Sm$_2$O$_3$ | | | 300 | 61.5 | 0 | 0 | 0 | 0 | 65.0 | 40.0 | 35.0 | 21.5 |
| 33 | Sm$_2$O$_3$ | | | 500 | 55.0 | 9.6 | 5.3 | 0 | 0 | 75.1 | 41.3 | 15.3 | 8.4 |
| 34 | Sm$_2$O$_3$ | | | 700 | 74.5 | 19.7 | 14.7 | 0 | 0 | 53.7 | 40.0 | 26.6 | 19.8 |
| 35 | Yb$_2$O$_3$ | | | 500 | 65.0 | 20.8 | 13.5 | 0 | 0 | 38.5 | 25.0 | 40.8 | 26.5 |
| 36 | Yb$_2$O$_3$ | | | 700 | 60.0 | 2.7 | 1.6 | 0 | 0 | 59.7 | 35.8 | 37.7 | 22.6 |
| 37 | Gd$_2$O$_3$ | | | 500 | 46.0 | 0 | 0 | 0 | 0 | 45.7 | 21.0 | 54.3 | 25.0 |
| 38 | Ho$_2$O$_3$ | | | 500 | 45.7 | 14.7 | 6.7 | 0 | 0 | 58.0 | 26.5 | 27.4 | 12.5 |
| 39 | Ho$_2$O$_3$ | | | 700 | 57.5 | 7.9 | 4.6 | 0 | 0 | 56.7 | 32.6 | 35.4 | 20.3 |
| 40 | Eu$_2$O$_3$ | | | 500 | 30.0 | 6.7 | 2.0 | 0 | 0 | 60.0 | 18.0 | 33.3 | 10.0 |
| 41 | Eu$_2$O$_3$ | | | 700 | 66.0 | 14.5 | 9.6 | 5.0 | 3.3 | 50.0 | 33.0 | 30.5 | 20.1 |
| 42 | Dy$_2$O$_3$ | | | 500 | 49.0 | 0 | 0 | 0 | 0 | 61.2 | 30.0 | 38.8 | 19.0 |
| 43 | Dy$_2$O$_3$ | | | 700 | 63.4 | 8.2 | 5.2 | 0 | 0 | 63.1 | 40.0 | 28.7 | 18.2 |
| 44 | Zr(OH)$_4$—Ca(OH)$_2$ | MEL XZO 691-01 | | 300 | 44.0 | 0 | 0 | 0 | 0 | 54.5 | 24.0 | 45.5 | 20.0 |
| 45 | Zr(OH)$_4$—Ca(OH)$_2$ | MEL XZO 691-01 | | 500 | 97.5 | 59.5 | 58.0 | 0 | 0 | 24.6 | 24.0 | 15.9 | 15.5 |
| 46 | Zr(OH)$_4$—Ca(OH)$_2$ | MEL XZO 691-01 | | 700 | 84.0 | 28.5 | 23.9 | 0 | 0 | 38.1 | 32.0 | 33.5 | 28.1 |
| 47 | Zr(OH)$_4$—Ca(OH)$_2$ | MEL XZO 691-01 | (1st Repeat) | 500 | 96.4 | 44.6 | 43.0 | 0 | 0 | 27.0 | 26.0 | 28.4 | 27.4 |
| 48 | Zr(OH)$_4$—Ca(OH)$_2$ | MEL XZO 691-01 | (2nd Repeat) | 500 | 66.4 | 30.1 | 20.0 | 0 | 0 | 39.2 | 26.0 | 30.7 | 20.4 |
| 49 | Zr(OH)$_4$—Ca(OH)$_2$ | MEL XZO 691-01 | (3rd Repeat) | 500 | 55.0 | 6.4 | 3.5 | 0 | 0 | 61.8 | 34.0 | 31.8 | 17.5 |
| 50 | Calcined Zr(OH)$_4$—Ca(OH)$_2$ (900 C.) | MEL XZO 691-01 | | 500 | 73.3 | 27.3 | 20.0 | 7.5 | 5.5 | 47.7 | 35.0 | 17.5 | 12.8 |
| 51 | Calcined Zr(OH)$_4$—Ca(OH)$_2$ (900 C.) | MEL XZO 691-01 | (1st Repeat) | 500 | 49.9 | 21.4 | 10.7 | 0 | 0 | 49.1 | 24.5 | 29.5 | 14.7 |
| 52 | Al-Doped ZrO$_2$ | MEL ALZ5C-4/D | | 500 | 100.0 | 48.7 | 48.7 | 0 | 0 | 28.6 | 28.6 | 22.7 | 22.7 |
| 53 | Al-Doped ZrO$_2$ | MEL ALZ5C-4/D | | 500 | 74.0 | 34.7 | 25.7 | 0 | 0 | 33.8 | 25.0 | 31.5 | 23.3 |
| 54 | Zr(OH)$_4$ | MEL FZ0922 | | 500 | 100.0 | 33.9 | 33.9 | 0 | 0 | 20.0 | 20.0 | 46.1 | 46.1 |
| 55 | Zr(OH)$_4$ | MEL FZ0922 | | 700 | 83.5 | 35.9 | 30.0 | 0 | 0 | 49.1 | 41.0 | 15.0 | 12.5 |
| 56 | Ce-Doped ZrO$_2$ | MEL 802 | | 500 | 50.4 | 26.8 | 13.5 | 0 | 0 | 48.2 | 24.3 | 25.0 | 12.6 |
| 57 | Ce-Doped ZrO$_2$ | MEL 802 | | 700 | 88.0 | 13.3 | 11.7 | 0 | 0 | 46.6 | 41.0 | 40.1 | 35.3 |
| 58 | Calcined La + Al Doped ZrO$_2$ (900 C.) | MEL ALZ22 | | 500 | 69.0 | 25.4 | 17.5 | 0 | 0 | 46.8 | 32.3 | 27.8 | 19.2 |
| 59 | Calcined La + Al Doped ZrO$_2$ (900 C.) | MEL ALZ22 | (1st Repeat) | 500 | 53.0 | 28.7 | 15.2 | 0 | 0 | 47.2 | 25.0 | 24.2 | 12.8 |
| 60 | Calcined La + Al Doped ZrO$_2$ (900 C.) | MEL ALZ22 | (2nd Repeat) | 500 | 63.0 | 21.7 | 13.7 | 0 | 0 | 50.0 | 31.5 | 28.3 | 17.8 |

TABLE 3-continued

Summary of pyroprobe runs for the conversion of BDO to 1,3BD

| Run | Catalyst | Descriptor | Notes | T (° C.) | BDO % Conv. | 1,3BD % Sel. | 1,3BD % Yield | MVC % Sel. | MVC % Yield | MEK % Sel. | MEK % Yield | Other % Sel. | Other % Yield |
|---|---|---|---|---|---|---|---|---|---|---|---|---|---|
| 61 | 8 mole % Y-Stab. ZrO$_2$ | Tosoh TZ-8YS | | 300 | 0 | 0 | 0 | 0 | 0 | 0 | 0 | 0 | 0 |
| 62 | 8 mole % Y-Stab. ZrO$_2$ | Tosoh TZ-8YS | | 500 | 38.0 | 0 | 0 | 0 | 0 | 56.8 | 21.6 | 43.2 | 16.4 |
| 63 | 10 mole % Y-Stab. ZrO$_2$ | Tosoh TZ-10YS | | 300 | 0 | 0 | 0 | 0 | 0 | 0 | 0 | 0 | 0 |
| 64 | 10 mole % Y-Stab. ZrO$_2$ | Tosoh TZ-10YS | | 500 | 28.0 | 10.0 | 2.8 | 0 | 0 | 50.7 | 14.2 | 39.3 | 11.0 |
| 65 | 13 mole % Y-Stab. ZrO$_2$ | Unitec Ceramics | | 300 | 0 | 0 | 0 | 0 | 0 | 0 | 0 | 0 | 0 |
| 66 | 13 mole % Y-Stab. ZrO$_2$ | Unitec Ceramics | | 500 | 38.0 | 0 | 0 | 0 | 0 | 16.6 | 6.3 | 83.4 | 31.7 |
| 67 | La + Al Doped ZrO$_2$ | MEL ALZ22 | | 500 | 88.0 | 63.6 | 56.0 | 31.0 | 27.3 | 0 | 0 | 5.3 | 4.7 |
| 68 | Ho$_2$O$_3$ | | | 300 | 11.0 | 0 | 0 | 0 | 0 | 0 | 0 | 100.0 | 11.0 |
| 69 | Ho$_2$O$_3$ | | | 500 | 7.0 | 0 | 0 | 0 | 0 | 0 | 0 | 100.0 | 7.0 |
| 70 | Ho$_2$O$_3$ | | | 700 | 40.0 | 0 | 0 | 0 | 0 | 60.8 | 24.3 | 39.3 | 15.7 |
| 71 | Y$_2$O$_3$ | | | 300 | 0 | 0 | 0 | 0 | 0 | 0 | 0 | 0 | 0 |
| 72 | Y$_2$O$_3$ | | | 500 | 0 | 0 | 0 | 0 | 0 | 0 | 0 | 0 | 0 |
| 73 | 3 mole % Y-Stab. ZrO$_2$ | Degussa VP 3-YSZ (40) | | 500 | 38.0 | 23.7 | 9.0 | 14.5 | 5.5 | 42.9 | 16.3 | 18.9 | 7.2 |
| 74 | 3 mole % Y-Stab. ZrO$_2$ | Degussa VP 3-YSZ (40) | | 500 | 37.1 | 21.0 | 7.8 | 11.1 | 4.1 | 42.6 | 15.8 | 25.3 | 9.4 |
| 75 | Y$_2$O$_3$ | | | 300 | 1.0 | 0 | 0 | 0 | 0 | 0 | 0 | 100.0 | 1.0 |
| 76 | Y$_2$O$_3$ | | | 500 | 6.0 | 0 | 0 | 0 | 0 | 0 | 0 | 100.0 | 6.0 |
| 77 | La$_2$O$_3$ | | | 500 | 8.0 | 0 | 0 | 0 | 0 | 0 | 0 | 100.0 | 8.0 |
| 78 | La$_2$O$_3$ | | | 700 | 23.2 | 0 | 0 | 0 | 0 | 53.0 | 12.3 | 47.0 | 10.9 |
| 79 | Nd$_2$O$_3$ | | | 500 | 5.0 | 0 | 0 | 0 | 0 | 0 | 0 | 100.0 | 5.0 |
| 80 | Nd$_2$O$_3$ | | | 700 | 33.0 | 20.6 | 6.8 | 10.3 | 3.4 | 48.5 | 16.0 | 20.6 | 6.8 |
| 81 | Ho$_2$O$_3$ | | | 500 | 6.0 | 0 | 0 | 0 | 0 | 0 | 0 | 100.0 | 6.0 |
| 82 | Ho$_2$O$_3$ | | | 700 | 40.0 | 0 | 0 | 0 | 0 | 78.3 | 31.3 | 21.8 | 8.7 |
| 83 | Er$_2$O$_3$ | | | 300 | 1.0 | 0 | 0 | 0 | 0 | 0 | 0 | 100.0 | 1.0 |
| 84 | Er$_2$O$_3$ | | | 500 | 13.0 | 30.8 | 4.0 | 0 | 0 | 31.5 | 4.1 | 37.7 | 4.9 |
| 85 | Er$_2$O$_3$ | | | 700 | 42.0 | 22.1 | 9.3 | 5.7 | 2.4 | 61.4 | 25.8 | 10.7 | 4.5 |
| 86 | Tm$_2$O$_3$ | | | 300 | 1.0 | 0 | 0 | 0 | 0 | 0 | 0 | 100.0 | 1.0 |
| 87 | Tm$_2$O$_3$ | | | 500 | 91.5 | 61.5 | 56.3 | 0 | 0 | 26.3 | 24.1 | 12.1 | 11.1 |
| 88 | Tm$_2$O$_3$ | | | 700 | 89.0 | 28.2 | 25.1 | 0 | 0 | 28.5 | 25.4 | 43.3 | 38.5 |
| 89 | Tb$_4$O$_7$ | | | 300 | 30.0 | 0 | 0 | 0 | 0 | 0 | 0 | 100.0 | 30.0 |
| 90 | Tb$_4$O$_7$ | | | 500 | 48.0 | 0 | 0 | 0 | 0 | 18.1 | 8.7 | 81.9 | 0 |
| 91 | Tb$_4$O$_7$ | | | 700 | 64.0 | 0 | 0 | 0 | 0 | 20.5 | 13.1 | 79.5 | 50.9 |
| 92 | Lu$_2$O$_3$ | | | 300 | 4.0 | 0 | 0 | 0 | 0 | 0 | 0 | 100.0 | 4.0 |
| 93 | Lu$_2$O$_3$ | | | 500 | 32.5 | 30.8 | 10.0 | 0 | 0 | 36.9 | 12.0 | 32.3 | 10.5 |
| 94 | Lu$_2$O$_3$ | | | 700 | 85.7 | 20.1 | 17.2 | 6.2 | 5.3 | 22.2 | 19.0 | 51.6 | 44.2 |
| 95 | Sc$_2$O$_3$ | | | 300 | 7.0 | 0 | 0 | 0 | 0 | 71.4 | 5.0 | 28.6 | 2.0 |
| 96 | Sc$_2$O$_3$ | | | 500 | 45.4 | 30.2 | 13.7 | 11.2 | 5.1 | 33.0 | 15.0 | 25.6 | 11.6 |
| 97 | Sc$_2$O$_3$ | | | 700 | 75.3 | 29.2 | 22.0 | 12.9 | 9.7 | 27.0 | 20.3 | 30.9 | 23.3 |
| 98 | HfO$_2$ | | | 300 | 4.0 | 0 | 0 | 0 | 0 | 0 | 0 | 100.0 | 4.0 |
| 99 | HfO$_2$ | | | 500 | 31.5 | 27.6 | 8.7 | 0 | 0 | 38.7 | 12.2 | 33.7 | 10.6 |
| 100 | HfO$_2$ | | | 700 | 40.0 | 0 | 0 | 0 | 0 | 78.3 | 31.3 | 21.8 | 8.7 |
| 101 | Pr$_6$O$_{11}$ | | | 300 | 4.0 | 0 | 0 | 0 | 0 | 0 | 0 | 100.0 | 4.0 |
| 102 | Pr$_6$O$_{11}$ | | | 500 | 73.0 | 0 | 0 | 0 | 0 | 11.0 | 8.0 | 89.0 | 65.0 |
| 103 | Pr$_6$O$_{11}$ | | | 700 | 68.0 | 0 | 0 | 0 | 0 | 17.1 | 11.6 | 82.9 | 56.4 |
| 104 | 50 mole % ZnO/ 50 mole % SiO$_2$ | | | 500 | 23.9 | 11.3 | 2.7 | 0 | 0 | 68.2 | 16.3 | 20.5 | 4.9 |
| 105 | 50 mole % ZnO/ 50 mole % SiO$_2$ | | | 700 | 40.5 | 15.3 | 6.2 | 0 | 0 | 60 | 24.3 | 24.7 | 10.0 |
| 106 | High Purity HfO$_2$ powder | Teledyne Wah Chang | 99.99% HfO$_2$ | 500 | 24.7 | 12.2 | 3.0 | 5.3 | 1.3 | 80.0 | 14.8 | 22.6 | 5.6 |
| 107 | High Purity HfO$_2$ powder | Teledyne Wah Chang | 99.99% HfO$_2$ | 700 | 67.5 | 9.8 | 6.6 | 4.7 | 3.2 | 60.0 | 40.5 | 25.5 | 17.2 |
| 108 | 3 mole % Sc Stabilised ZrO$_2$ | Praxair | | 500 | 14.7 | 10.2 | 1.5 | 3.4 | 0.5 | 58.6 | 8.6 | 27.8 | 4.1 |
| 109 | 3 mole % Sc Stabilised ZrO$_2$ | Praxair | | 700 | 68.5 | 14.6 | 10.0 | 1.9 | 1.3 | 57.2 | 39.2 | 26.3 | 18.0 |
| 110 | 10 wt % Tm$_2$O$_3$ on Aerosil 380 | | | 500 | 65.8 | 11.6 | 7.6 | 0 | 0 | 62.6 | 41.2 | 25.8 | 17.0 |
| 111 | 10 wt % Tm$_2$O$_3$ on Aerosil 380 | | | 700 | 79.4 | 13.4 | 10.6 | 0 | 0 | 61.5 | 48.8 | 25.2 | 20.0 |
| 112 | Ta$_2$O$_5$ -325 mesh powder | Cerac T-1013 | | 500 | 17.8 | 10.1 | 0 | 0 | 0 | 58.4 | 0 | 31.5 | 5.6 |
| 113 | La + Al Doped ZrO$_2$ | MEL ALZ22 | | 500 | 94.8 | 57.0 | 54.0 | 0 | 0 | 32.1 | 30.4 | 11.0 | 10.4 |
| 114 | La + Al Doped ZrO$_2$ | MEL ALZ22 | | 700 | 100.0 | 0 | 0 | 0 | 0 | 0 | 0 | 100.0 | 100.0 |
| 115 | La + Al Doped ZrO$_2$ | MEL FZO2089 | MEL ALZ22 Equivalent | 500 | 84.0 | 56.0 | 47.0 | 0 | 0 | 30.4 | 25.5 | 13.7 | 11.5 |
| 116 | La + Al Doped ZrO$_2$ | MEL FZO2089 | MEL ALZ22 Equivalent | 700 | 89.8 | 24.5 | 22.0 | 0 | 0 | 55.7 | 50.0 | 19.8 | 17.8 |
| 117 | Calcined La + Al Doped ZrO$_2$ (550 C.) | MEL FZO2089 | | 500 | 92.5 | 51.9 | 48.0 | 0 | 0 | 25.4 | 23.5 | 22.7 | 21.0 |

TABLE 3-continued

Summary of pyroprobe runs for the conversion of BDO to 1,3BD

| Run | Catalyst | Descriptor | Notes | T (° C.) | BDO % Conv. | 1,3BD % Sel. | 1,3BD % Yield | MVC % Sel. | MVC % Yield | MEK % Sel. | MEK % Yield | Other % Sel. | Other % Yield |
|---|---|---|---|---|---|---|---|---|---|---|---|---|---|
| 118 | Calcined La + Al Doped $ZrO_2$ (550 C.) | MEL FZO2089 | | 700 | 87.1 | 47.1 | 41.0 | 0 | 0 | 36.2 | 31.5 | 16.8 | 14.6 |
| 119 | Calcined La + Al Doped $ZrO_2$ (650 C.) | MEL FZO2089 | | 500 | 92.9 | 57.9 | 53.8 | 0 | 0 | 23.1 | 21.5 | 18.9 | 17.6 |
| 120 | Calcined La + Al Doped $ZrO_2$ (650 C.) | MEL FZO2089 | | 700 | 87.4 | 47.3 | 41.3 | 0 | 0 | 34.3 | 30.0 | 18.4 | 16.1 |
| 121 | Boron Oxide Glass | | | 500 | 56.9 | 5.3 | 3.0 | 0 | 0 | 101.9 | 58.0 | −7.2 | −4.1 |

Example 2

High Throughput Catalyst Testing

Catalysts for high throughput testing were either commercially available catalysts, commercially available catalysts that had been modified, or catalysts prepared in-house. Catalysts (50 mg) were loaded into tapered reactor tubes, with an OD of 3 mm, ID of 2.6 mm, and length of 300 mm. When loading the reactors, a small portion of Zirblast® (ceramic beads comprising 68-70% $ZrO_2$, 28-33% $SiO_2$, and <10% $Al_2O_3$, with a crystal structure of 68% zirconia and 32% vitreous phase, specific gravity 3.85 g/cm$^3$, bulk density 2.3 kg/L, Saint-Gobain, France) was added to the bottom of each reactor. Pre-weighed portions of the catalyst were added to each tube. The remaining volume of the tube was filled with Zirblast® and plugged with quartz wool.

The catalysts were activated by heating at 10° C./min to a temperature of 425° C. with a 12.5 mL/min He flow rate at ambient pressure, After a 2-hour hold, each reactor block was cooled to the target reaction temperature. The He flow was reduced to 1 mL/min and flow of neat BDO was then started at 0.01 mL/min. The liquid collection autosampler was cooled to 4° C. After a 10 minute wait at the reaction conditions, collection of sample set #1 began. For liquid collection, the outlet gases were bubbled through a trapping solvent of dimethyl diglyme containing an internal standard of about 0.5% 1-octanol (3 mL per vial). Liquid sampling for this and each subsequent condition was done over a 3 hour period. On-line gas GC analysis was performed at the beginning and end of the sampling time. Upon completion of liquid sampling at the first condition, the sample vial was replaced, the reactor conditions were changed, and sample set #2 was started in the same manner following a 10 min wait period. All liquid samples were weighed after the run. Samples were diluted and run on a GC-FID.

Table 4 shows the catalysts present in each run. Tables 5-34 show the screening results.

TABLE 4

| | | | Screening 1 |
|---|---|---|---|
| 1 | 1-1 | $La_2O_3/Al_2O_3/ZrO_2$ | MEL Chemicals, Inc. (MEL) FZO2089 |
| 2 | 1-2 | $Tm_2O_3$ | oxide via nitrate decomposition |
| 3 | 1-3 | $Tm_2O_3$ | oxide via oxalate decomposition |
| 4 | 1-4 | $Tm_2O_3$ | oxide on $Zr(OH)_4$ support - dried |
| 5 | 1-5 | $Tm_2O_3$ | oxide on $Zr(OH)_4$ support - calcined |
| 6 | 1-6 | $Tm_2O_3$ | oxide on calcined $Zr(OH)_4$ support - recalcined |
| 7 | 1-7 | $La_2O_3/ZrO_2$ | MEL XZO945-03 10% La-doped $ZrO_2$, calcined 600° C. |
| 8 | 1-8 | Ca-doped $ZrO_2$ | MEL XZ0691-01. calcined 900° C. |
| | | | Screening 2 |
| 1 | 2-1 | $SC_2O_3$ | oxide via nitrate decomp |
| 2 | 2-2 | $La_2O_3/Al_2O_3/ZrO_2$ | MEL FZO2089 |
| 3 | 2-3 | $SC_2O_3$ | oxide on $Zr(OH)_4$ support - dried |
| 4 | 2-4 | $SC_2O_3$ | oxide on $Zr(OH)_4$ support - calcined |
| 5 | 2-5 | $Dy_2O_3$ | oxide via nitrate decomp |
| 6 | 2-6 | $ZrO_2$ | MEL XZO1501-06 as received |
| 7 | 2-7 | $ZrO_2$ | MEL XZO1501-09 as received |
| 8 | 2-8 | $ZrO_2$ | MEL XZO1501-06 calcined |
| | | | Screening 3 |
| 1 | 3-1 | $La_2O_3/Zr_2O_3$ | MEL XZO945-03 10% La-doped $ZrO_2$, calcined 600 C. |
| 2 | 3-2 | $Er_2O_3$ | oxide on $Zr(OH)_4$ support - dried |
| 3 | 3-3 | $Er_2O_3$ | oxide on $Zr(OH)4$ support - calcined |
| 4 | 3-4 | $La_2O_3$ | oxide on $Zr(OH)_4$ support - dried |
| 5 | 3-5 | $La_2O_3$ | oxide on $Zr(OH)_4$ support - calcined |
| 6 | 3-6 | $Lu_2O_3$ | oxide on $Zr(OH)_4$ support - dried |
| 7 | 3-7 | $Lu_2O_3$ | oxide on $Zr(OH)_4$ support - calcined |
| 8 | 3-9 | ZnO | oxide on $Zr(OH)_4$ support - calcined |
| | | | Screening 4 and Screening 4 Repeat |
| 1 | 4-1 | $La_2O_3/Zr_2O_3$ | XZO945-03 10% La-doped $ZrO_2$, calcined 600 C. |
| 2 | 4-2 | $ZrO_2$ | oxide on $Zr(OH)_4$ support - dried |
| 3 | 4-3 | $ZrO_2$ | oxide on $Zr(OH)_4$ support - calcined |
| 4 | 4-4 | $In_2O_3$ | oxide via oxalate decomposition, oxalic acid preparation |

TABLE 4-continued

| | | | |
|---|---|---|---|
| 5 | 4-5 | $In_2O_3$ | oxide on $Zr(OH)_4$ support - calcined |
| 6 | 4-6 | $Lu_2O_3$ | Ca-doped oxide via oxalate |
| 7 | 4-7 | $Lu_2O_3$ | oxide via nitrate decomposition |
| 8 | 4-8 | $Er_2O_3$ | oxide on calcined $Zr(OH)_4$ support - recalcined |
| 9 | 4-9 | $Er_2O_3$ | oxide on calcined $Zr(OH)_4$ support - recalcined |
| 10 | 4-10 | $Y_2O_3$ | oxide via oxalate decomposition |
| 11 | 4-11 | $Y_2O_3$ | oxide via nitrate decomposition |
| 12 | 4-12 | $Y_2O_3$ | Ca-doped oxide via oxalate |
| 13 | 4-13 | $Ba_3(PO_4)_2$ | phosphate co-ppt, dried |
| 14 | 4-14 | $LiCaPO_4$ | phosphate co-ppt, dried |
| 15 | 4-15 | $BPO_4$ | phosphate co-ppt, calcined |
| 16 | 4-16 | $Mg_3(PO_4)_2$ | phosphate co-ppt, calcined |
| | | Screening 5 | |
| 1 | 5-1 | $La_2O_3/ZrO_2$ | MEL XZO945-03 10% La-doped $ZrO_2$, calcined 600° C. |
| 2 | 5-2 | $Er_2O_3$ | oxide via nitrate decomposition |
| 3 | 5-3 | $Er_2O_3$ | oxide via nitrate decomposition |
| 4 | 5-4 | $Gd_2O$ | oxide via nitrate decomposition |
| 5 | 5-5 | $HO_2O_3$ | oxide via nitrate decomposition |
| 6 | 5-6 | $La_2O_3$ | oxide via nitrate decomposition |
| 7 | 5-7 | $Nd_2O_3$ | oxide via nitrate decomposition |
| 8 | 5-8 | $Pr_eO_{11}$ | oxide via nitrate decomposition |
| 9 | 5-9 | $Sm_2O_3$ | oxide via nitrate decomposition |
| 10 | 5-10 | $Tb_4O_7$ | oxide via nitrate decomposition |
| 11 | 5-11 | $Yb_2O_3$ | oxide via nitrate decomposition |
| 12 | 5-12 | $MgAl_2O_4$ | oxide via nitrate decomposition |
| 13 | 5-13 | Ca-doped $CeO_2$ | oxide via nitrate decomposition |
| 14 | 5-14 | MoOHD 3 | oxide via AFIM decomposition |
| 15 | 5-15 | $HfO2$ | oxide via hydroxide decomposition |
| 16 | 5-16 | $CeO_2/ZrO_2$ | MEL 802 |
| | | Screening 6 | |
| 1 | 6-1 | $La_2O_3/ZrO_2$ | MEL XZO945-03 10% La-doped $ZrO_2$, calcined 600 C. |
| 2 | 6-2 | $Al/ZrO_2$ | MEL ALZ5C-4/D |
| 3 | 6-3 | $Ca/ZrO_2$ | MEL XZO691-01 |
| 4 | 6-4 | $WO_3/ZrO_2$ | MEL XZO1251-01 |
| 5 | 6-5 | $CeO_2/La_2O_3/ZrO_2$ | MEL XZO892-02 |
| 6 | 6-6 | $SiO_2/ZrO_2$ | MEL XZO645-01 |
| 7 | 6-7 | $CeO_2/La_2O_3/ZrO_2$ | MEL XZO1291-01 (high porosity) |
| 8 | 6-8 | $La_2O_3/ZrO_2$ | MEL XZO945-3 |
| 9 | 6-9 | $La_2O_3/ZrO_2$ | 900° C. calcined |
| 10 | 6-10 | $Zr(OH)_4$ | MEL XZO922 |
| 11 | 6-11 | $In_2O_3$ | 900° C. calcined ($In_2O_3$ from oxalic acid preparation) |
| 12 | 6-12 | $Er_2O_3$ | 900° C. calcined |
| 13 | 6-13 | $Yb_2O_3$ | 900° C. calcined |
| 14 | 6-14 | $Tm/ZrO_2$ | 900° C. calcined |
| 15 | 6-15 | $Lu_2O_3/ZrO_2$ | 900° C. calcined |
| 16 | 6-16 | $SC_2O_3/ZrO_2$ | 900° C. calcined |
| | | Screening 7 - (MVC to BD) | |
| 1 | 7-1 | $Ba_3(PO_4)_2$ | |
| 2 | 7-2 | $LiCaPO_4$ | |
| 3 | — | — | (no flow during expt) |
| 4 | 7-4 | $Mg_3(PO_4)_2$ | |
| 5 | — | — | |
| 6 | — | — | (no flow during expt) |
| 7 | 7-7 | ZSM-5 (30) | |
| 8 | 7-8 | beta zeolite | |
| 9 | — | — | (no flow during expt) |
| 10 | — | — | (no flow during expt) |
| 11 | 7-11 | | Grace Davicat ® SIAL 3111 silica-alumina (13% $Al_2O_3$), 475 $m^2/g$, 1.1 mL/g, 74 μm average pore size |
| 12 | 7-12 | | Grace Davicat ® SIAL 3113 silica-alumina (13% $Al_2O_3$), 573 $m^2/g$, 0.76 mL/g, 73 μm average pore size |
| 13 | 7-13 | | Grace Davicat ® SIAL 3115 silica-alumina (13% $Al_2O_3$), 360 m2/g, 1.2 mL/g, 68 μm average pore size |
| 14 | 7-14 | | Grace Davicat ® SIAL 3125 silica-alumina (25% $Al_2O_3$), 552 $m^2/g$, 0.79 mL/g, 78 μm average pore size |
| 15 | 7-15 | $Al_2O_3$ | Engelhard 4126 |
| 16 | 7-16 | $Al_2O_3$ | Grace AL2200 Alumina |

TABLE 5

| Screening 1, 300° C., 3 h | | | | | | | | |
|---|---|---|---|---|---|---|---|---|
| Catalyst: | 1-1 | 1-2 | 1-3 | 1-4 | 1-5 | 1-6 | 1-7 | 1-8 |
| BDO Conversion | 68.0% | 34.2% | 19.5% | 24.1% | 15.4% | 12.5% | 18.4% | — |
| 1,3 butadiene | 0.1% | 0.0% | 0.0% | 0.0% | 0.0% | 0.0% | 0.0% | 0.0% |
| butenes | 0.0% | 0.0% | 0.0% | 0.0% | 0.0% | 0.0% | 0.0% | 0.0% |
| 4-vinyl-1-cyclohexene | 0.2% | 0.0% | 0.2% | 0.2% | 0.2% | 0.2% | 0.2% | 0.2% |
| acetone | 0.3% | 0.0% | 0.0% | 0.0% | 0.0% | 0.0% | 0.0% | 0.0% |
| isobutyraldehyde | 1.3% | 0.0% | 0.0% | 0.0% | 0.0% | 0.0% | 0.0% | 0.0% |
| 2,3-butanedione | 0.7% | 0.1% | 0.1% | 0.4% | 0.3% | 0.2% | 0.5% | 0.2% |
| MEK | 23.6% | 0.5% | 0.1% | 1.7% | 1.3% | 0.6% | 1.0% | 0.7% |
| acetoin | 3.1% | 0.4% | 0.3% | 1.4% | 0.8% | 0.7% | 0.9% | 0.0% |
| MVC | 5.9% | 0.0% | 0.0% | 3.0% | 1.4% | 1.3% | 1.5% | 0.0% |
| isobutanol | 2.5% | 0.1% | 0.1% | 1.2% | 0.5% | 0.3% | 0.5% | 0.0% |
| Total | 37.7% | 1.2% | 0.9% | 7.9% | 4.5% | 3.3% | 4.6% | 1.1% |

TABLE 6

| Screening 1 (cont'd), 300° C., 6 h | | | | | | | | |
|---|---|---|---|---|---|---|---|---|
| Catalyst: | 1-1 | 1-2 | 1-3 | 1-4 | 1-5 | 1-6 | 1-7 | 1-8 |
| BDO Conversion | 64.0% | 22.9% | 10.1% | 8.7% | 8.1% | 2.3% | 4.4% | — |
| 1,3 butadiene | 0.1% | 0.0% | 0.0% | 0.0% | 0.0% | 0.0% | 0.0% | 0.0% |
| butenes | 0.0% | 0.0% | 0.0% | 0.0% | 0.0% | 0.0% | 0.0% | 0.0% |
| 4-vinyl-1-cyclohexene | 0.0% | 0.0% | 0.0% | 0.0% | 0.0% | 0.0% | 0.0% | 0.0% |
| acetone | 1.0% | 0.0% | 0.0% | 0.0% | 0.0% | 0.0% | 0.0% | 0.0% |
| isobutyraldehyde | 1.0% | 0.0% | 0.0% | 0.0% | 0.0% | 0.0% | 0.0% | 0.0% |
| 2,3-butanedione | 0.6% | 0.1% | 0.1% | 0.3% | 0.3% | 0.2% | 0.3% | 0.1% |
| MEK | 17.9% | 0.3% | 0.5% | 1.5% | 1.1% | 0.6% | 0.8% | 0.6% |
| acetoin | 2.5% | 0.4% | 0.3% | 1.6% | 0.7% | 0.8% | 0.7% | 0.0% |
| MVC | 4.6% | 0.0% | 0.0% | 3.0% | 1.3% | 1.4% | 1.1% | 0.0% |
| isobutanol | 1.8% | 0.0% | 0.0% | 1.2% | 0.5% | 0.3% | 0.4% | 0.0% |
| Total | 29.5% | 0.9% | 0.9% | 7.6% | 3.9% | 3.2% | 3.2% | 0.7% |

TABLE 7

| Screening 1 (cont'd), 350° C., 3 h | | | | | | | | |
|---|---|---|---|---|---|---|---|---|
| Catalyst: | 1-1 | 1-2 | 1-3 | 1-4 | 1-5 | 1-6 | 1-7 | 1-8 |
| BDO Conversion | 100.0% | 36.2% | 41.8% | 89.1% | 71.6% | 59.3% | 66.6% | 15.1% |
| 1,3 butadiene | 0.7% | 0.1% | 0.0% | 0.1% | 0.1% | 0.1% | 0.1% | 0.1% |
| butenes | 0.1% | 0.1% | 0.1% | 0.2% | 0.1% | 0.2% | 0.1% | 0.1% |
| 4-vinyl-1-cyclohexene | 0.2% | 0.3% | 0.2% | 0.5% | 0.3% | 0.3% | 0.3% | 0.2% |
| acetone | 2.2% | 0.3% | 0.2% | 2.2% | 0.9% | 0.8% | 1.1% | 0.9% |
| isobutyraldehyde | 2.2% | 0.3% | 0.2% | 2.2% | 0.9% | 0.8% | 1.1% | 0.9% |
| 2,3-butanedione | 0.7% | 1.0% | 0.7% | 2.1% | 1.5% | 1.4% | 2.0% | 1.0% |
| MEK | 28.4% | 4.7% | 5.0% | 21.0% | 11.5% | 7.8% | 10.3% | 5.3% |
| acetoin | 3.3% | 3.7% | 2.3% | 0.1% | 0.1% | 0.1% | 9.7% | 0.3% |
| MVC | 0.8% | 1.6% | 0.6% | 3.6% | 10.7% | 0.5% | 9.9% | 0.6% |
| isobutanol | 5.0% | 1.4% | 1.2% | 15.3% | 7.3% | 5.1% | 7.4% | 0.1% |
| Total | 43.6% | 13.2% | 10.6% | 47.2% | 33.3% | 16.9% | 42.2% | 9.5% |

TABLE 8

| Screening 1 (cont'd), 350° C., 6 h | | | | | | | | |
|---|---|---|---|---|---|---|---|---|
| Catalyst: | 1-1 | 1-2 | 1-3 | 1-4 | 1-5 | 1-6 | 1-7 | 1-8 |
| BDO Conversion | 96.4% | 21.2% | 26.6% | 82.5% | 62.7% | 60.6% | 55.4% | 3.6% |
| 1,3 butadiene | 0.4% | 0.0% | 0.0% | 0.1% | 0.1% | 0.1% | 0.1% | 0.0% |
| butenes | 0.1% | 0.1% | 0.1% | 0.1% | 0.1% | 0.1% | 0.1% | 0.1% |
| 4-vinyl-1-cyclohexene | 0.1% | 0.0% | 0.0% | 0.3% | 0.0% | 0.0% | 0.0% | 0.0% |
| acetone | 1.6% | 0.0% | 0.2% | 2.2% | 1.1% | 0.6% | 0.8% | 0.7% |

TABLE 8-continued

Screening 1 (cont'd), 350° C., 6 h

| Catalyst: | 1-1 | 1-2 | 1-3 | 1-4 | 1-5 | 1-6 | 1-7 | 1-8 |
|---|---|---|---|---|---|---|---|---|
| isobutyraldehyde | 1.6% | 0.0% | 0.2% | 2.2% | 1.1% | 0.6% | 0.8% | 0.7% |
| 2,3-butanedione | 0.6% | 0.9% | 0.9% | 2.1% | 1.7% | 1.3% | 1.9% | 0.8% |
| MEK | 22.2% | 3.5% | 4.4% | 19.5% | 11.8% | 6.4% | 8.0% | 3.8% |
| acetoin | 4.3% | 3.2% | 2.3% | 0.1% | 0.1% | 8.4% | 8.7% | 0.3% |
| MVC | 4.6% | 1.6% | 0.7% | 19.0% | 14.3% | 13.1% | 9.4% | 0.5% |
| isobutanol | 4.9% | 1.1% | 1.1% | 15.8% | 8.9% | 4.5% | 6.2% | 0.0% |
| Total | 40.3% | 10.3% | 9.8% | 61.3% | 39.1% | 35.1% | 36.0% | 7.0% |

TABLE 9

Screening 2, 300° C., 3 h

| Catalyst: | 2-1 | 2-2 | 2-3 | 2-4 | 2-5 | 2-6 | 2-7 | 2-8 |
|---|---|---|---|---|---|---|---|---|
| BDO Conversion | 100.0% | 84.4% | 100.0% | 100.0% | 100.0% | 100.0% | 100.0% | 100.0% |
| 1,3 butadiene | 0.0% | 0.1% | 0.0% | 0.0% | 0.0% | 0.0% | 0.0% | 0.0% |
| butenes | 0.0% | 0.0% | 0.0% | 0.0% | 0.0% | 0.0% | 0.0% | 0.0% |
| 4-vinyl-1-cyclohexene | 0.0% | 0.2% | 2.2% | 2.4% | 2.3% | 2.2% | 2.6% | 2.1% |
| acetone | 2.3% | 0.7% | 0.0% | 0.0% | 0.0% | 0.2% | 0.2% | 0.0% |
| isobutyraldehyde | 0.0% | 0.7% | 0.0% | 0.0% | 0.0% | 0.2% | 0.2% | 0.0% |
| 2,3-butanedione | 0.2% | 0.3% | 0.3% | 0.3% | 0.3% | 0.3% | 0.4% | 0.3% |
| MEK | 0.8% | 22.2% | 1.6% | 1.5% | 1.1% | 1.8% | 2.6% | 1.2% |
| acetoin | 0.5% | 2.3% | 1.6% | 1.1% | 0.4% | 1.6% | 2.3% | 0.9% |
| MVC | 3.5% | 3.8% | 2.2% | 1.8% | 0.0% | 4.0% | 5.1% | 2.1% |
| isobutanol | 0.2% | 2.8% | 1.2% | 0.8% | 0.2% | 1.4% | 2.1% | 0.7% |
| Total | 7.5% | 33.1% | 9.1% | 8.0% | 4.3% | 11.6% | 15.5% | 7.3% |

TABLE 10

Screening 2 (cont'd), 300° C., 6 h

| Catalyst: | 2-1 | 2-2 | 2-3 | 2-4 | 2-5 | 2-6 | 2-7 | 2-8 |
|---|---|---|---|---|---|---|---|---|
| BDO Conversion | 100.0% | 77.8% | 100.0% | 100.0% | 100.0% | 100.0% | 100.0% | 100.0% |
| 1,3 butadiene | 0.0% | 0.1% | 0.0% | 0.0% | 0.0% | 0.0% | 0.0% | 0.0% |
| butenes | 0.0% | 0.0% | 0.0% | 0.0% | 0.0% | 0.0% | 0.0% | 0.0% |
| 4-vinyl-1-cyclohexene | 0.2% | 0.2% | 0.2% | 0.2% | 0.2% | 0.3% | 0.2% | 0.2% |
| acetone | 0.0% | 0.5% | 0.0% | 0.0% | 0.0% | 0.2% | 0.2% | 0.0% |
| isobutyraldehyde | 0.0% | 0.5% | 0.0% | 0.0% | 0.0% | 0.2% | 0.2% | 0.0% |
| 2,3-butanedione | 0.2% | 0.3% | 0.3% | 0.3% | 0.2% | 0.4% | 0.3% | 0.2% |
| MEK | 0.7% | 17.2% | 1.3% | 1.2% | 0.8% | 1.8% | 1.8% | 0.9% |
| acetoin | 0.5% | 2.0% | 1.5% | 1.0% | 0.5% | 1.8% | 1.8% | 0.8% |
| MVC | 3.1% | 3.2% | 2.0% | 1.7% | 0.0% | 4.5% | 3.9% | 1.8% |
| isobutanol | 0.2% | 2.2% | 1.0% | 0.7% | 0.1% | 1.4% | 1.4% | 0.5% |
| Total | 4.8% | 26.3% | 6.3% | 5.1% | 1.9% | 10.4% | 9.8% | 4.4% |

TABLE 11

Screening 2 (cont'd), 350° C., 3 h

| Catalyst: | 2-1 | 2-2 | 2-3 | 2-4 | 2-5 | 2-6 | 2-7 | 2-8 |
|---|---|---|---|---|---|---|---|---|
| BDO Conversion | 100.0% | 98.0% | 95.7% | 74.9% | 100.0% | 100.0% | 97.1% | 92.5% |
| 1,3 butadiene | 0.1% | 1.0% | 0.1% | 0.1% | 0.1% | 0.1% | 0.1% | 0.1% |
| butenes | 0.1% | 0.1% | 0.0% | 0.1% | 0.1% | 0.1% | 0.1% | 0.2% |
| 4-vinyl-1-cyclohexene | 2.0% | 2.0% | 2.4% | 2.6% | 2.7% | 2.8% | 2.3% | 1.6% |
| acetone | 0.5% | 3.7% | 2.6% | 1.1% | 0.4% | 2.9% | 2.8% | 1.3% |
| isobutyraldehyde | 0.5% | 3.7% | 2.6% | 1.1% | 0.4% | 2.9% | 2.8% | 1.3% |
| 2,3-butanedione | 0.9% | 1.1% | 1.3% | 1.7% | 1.3% | 1.8% | 1.9% | 0.9% |
| MEK | 5.9% | 48.6% | 21.5% | 18.0% | 6.9% | 24.3% | 24.8% | 13.6% |
| acetoin | 3.6% | 0.0% | 0.0% | 0.0% | 5.3% | 0.0% | 0.0% | 0.0% |

TABLE 11-continued

Screening 2 (cont'd), 350° C., 3 h

| Catalyst: | 2-1 | 2-2 | 2-3 | 2-4 | 2-5 | 2-6 | 2-7 | 2-8 |
|---|---|---|---|---|---|---|---|---|
| MVC | 13.3% | 1.5% | 0.9% | 13.4% | 1.3% | 3.2% | 3.8% | 10.5% |
| isobutanol | 2.3% | 8.0% | 15.4% | 9.3% | 2.2% | 17.5% | 15.9% | 9.1% |
| Total | 29.2% | 69.7% | 46.8% | 47.5% | 20.6% | 55.7% | 54.5% | 38.7% |

TABLE 12

Screening 2 (cont'd), 350° C., 6 h

| Catalyst: | 2-1 | 2-2 | 2-3 | 2-4 | 2-5 | 2-6 | 2-7 | 2-8 |
|---|---|---|---|---|---|---|---|---|
| BDO Conversion | 100.0% | 100.0% | 100.0% | 100.0% | 100.0% | 100.0% | 100.0% | 100.0% |
| 1,3 butadiene | 0.1% | 0.7% | 0.1% | 0.1% | 0.0% | 0.1% | 0.1% | 0.1% |
| butenes | 0.1% | 0.1% | 0.0% | 0.1% | 0.1% | 0.1% | 0.1% | 0.2% |
| 4-vinyl-1-cyclohexene | 0.2% | 0.3% | 0.4% | 0.3% | 0.3% | 0.5% | 0.6% | 0.2% |
| acetone | 0.4% | 3.2% | 2.0% | 1.1% | 0.2% | 2.6% | 2.9% | 0.9% |
| isobutyraldehyde | 0.4% | 3.2% | 2.0% | 1.1% | 0.2% | 2.6% | 2.9% | 0.9% |
| 2,3-butanedione | 0.7% | 1.5% | 1.1% | 1.8% | 1.1% | 1.8% | 2.4% | 0.8% |
| MEK | 4.5% | 43.7% | 16.0% | 14.6% | 5.0% | 20.2% | 23.6% | 9.9% |
| acetoin | 2.4% | 0.0% | 0.0% | 10.9% | 4.3% | 0.0% | 0.0% | 7.2% |
| MVC | 9.0% | 2.1% | 8.3% | 14.3% | 1.1% | 3.8% | 4.8% | 9.6% |
| isobutanol | 2.0% | 8.6% | 12.6% | 9.0% | 1.5% | 16.7% | 17.4% | 6.7% |
| Total | 19.8% | 63.5% | 42.5% | 53.2% | 13.8% | 48.4% | 54.7% | 36.5% |

TABLE 13

Screening 3, 350° C., 3 h

| Catalyst: | 3-1 | 3-2 | 3-3 | 3-4 | 3-5 | 3-6 | 3-7 | 3-8 |
|---|---|---|---|---|---|---|---|---|
| BDO Conversion | 98.4% | 88.7% | 75.8% | 84.2% | 72.6% | 89.7% | 67.3% | 75.6% |
| 1,3 butadiene | 0.3% | 0.1% | 0.1% | 0.1% | 0.1% | 0.1% | 0.1% | 0.1% |
| butenes | 0.2% | 0.1% | 0.1% | 0.1% | 0.1% | 0.1% | 0.1% | 0.1% |
| 4-vinyl-1-cyclohexene | 0.0% | 0.0% | 0.0% | 0.0% | 0.0% | 0.0% | 0.0% | 0.0% |
| acetone | 1.5% | 2.4% | 1.9% | 2.5% | 2.2% | 2.3% | 2.0% | 2.0% |
| isobutyraldehyde | 2.5% | 1.7% | 0.5% | 1.9% | 1.0% | 1.9% | 0.5% | 0.9% |
| 2,3-butanedione | 0.0% | 3.4% | 2.4% | 3.6% | 3.4% | 4.0% | 3.2% | 3.4% |
| MEK | 17.5% | 21.7% | 13.8% | 21.2% | 15.7% | 22.5% | 14.7% | 17.3% |
| acetoin | 3.6% | 13.3% | 10.5% | 14.0% | 11.9% | 12.8% | 12.1% | 12.2% |
| MVC | 2.2% | 13.5% | 8.7% | 14.4% | 12.0% | 15.2% | 12.3% | 17.7% |
| isobutanol | 11.0% | 15.1% | 8.2% | 14.3% | 9.6% | 15.4% | 8.6% | 10.7% |
| 2-butanol | 2.2% | 3.2% | 2.5% | 2.5% | 2.1% | 3.0% | 2.1% | 1.6% |
| 2-buteneol | 0.0% | 0.0% | 0.0% | 0.0% | 0.0% | 0.0% | 0.0% | 0.0% |
| unknown | 2.2% | 1.9% | 1.3% | 1.6% | 1.3% | 1.4% | 1.0% | 1.1% |
| Total | 38.9% | 71.3% | 46.2% | 72.1% | 56.0% | 74.4% | 53.6% | 64.4% |

TABLE 14

Screening 3 (cont'd), 350° C., 6 h

| Catalyst: | 3-1 | 3-2 | 3-3 | 3-4 | 3-5 | 3-6 | 3-7 | 3-8 |
|---|---|---|---|---|---|---|---|---|
| BDO Conversion | 95.2% | 77.5% | 61.9% | 71.1% | 59.9% | 79.0% | 53.6% | 60.6% |
| 1,3 butadiene | 0.1% | 0.1% | 0.1% | 0.1% | 0.1% | 0.1% | 0.1% | 0.1% |
| butenes | 0.1% | 0.1% | 0.1% | 0.1% | 0.1% | 0.1% | 0.1% | 0.1% |
| 4-vinyl-1-cyclohexene | 0.0% | 0.0% | 0.0% | 0.0% | 0.0% | 0.0% | 0.0% | 0.0% |
| acetone | 0.0% | 0.0% | 0.0% | 0.0% | 0.0% | 0.0% | 0.0% | 0.0% |
| isobutyraldehyde | 1.9% | 1.4% | 0.0% | 1.4% | 0.8% | 1.6% | 0.0% | 0.7% |
| 2,3-butanedione | 0.0% | 3.4% | 2.4% | 3.6% | 3.4% | 4.1% | 3.1% | 3.3% |
| MEK | 11.4% | 17.4% | 9.9% | 16.8% | 11.7% | 19.4% | 10.8% | 14.0% |
| acetoin | 3.7% | 16.3% | 11.4% | 15.5% | 12.1% | 16.6% | 12.0% | 13.1% |
| MVC | 1.8% | 14.8% | 9.6% | 15.0% | 12.3% | 17.2% | 12.7% | 18.9% |
| isobutanol | 8.1% | 14.2% | 7.7% | 12.8% | 8.6% | 15.2% | 7.8% | 9.9% |
| 2-butanol | 1.6% | 2.5% | 2.0% | 1.9% | 1.6% | 2.4% | 1.5% | 1.3% |

TABLE 14-continued

Screening 3 (cont'd), 350° C., 6 h

| Catalyst: | 3-1 | 3-2 | 3-3 | 3-4 | 3-5 | 3-6 | 3-7 | 3-8 |
|---|---|---|---|---|---|---|---|---|
| 2-buteneol | 0.0% | 0.0% | 0.0% | 0.0% | 0.0% | 0.0% | 0.0% | 0.0% |
| unknown | 1.1% | 1.0% | 0.4% | 1.2% | 0.8% | 1.1% | 0.6% | 0.8% |
| Total | 27.1% | 67.6% | 41.2% | 65.3% | 49.2% | 74.2% | 46.4% | 60.0% |

TABLE 15

Screening 3 (cont'd), 400° C., 3 h

| Catalyst: | 3-1 | 3-2 | 3-3 | 3-4 | 3-5 | 3-6 | 3-7 | 3-8 |
|---|---|---|---|---|---|---|---|---|
| BDO Conversion | 100.0% | 100.0% | 100.0% | 100.0% | 100.0% | 100.0% | 100.0% | 100.0% |
| 1,3 butadiene | 2.4% | 2.4% | 2.4% | 2.5% | 7.5% | 2.7% | 2.0% | 3.2% |
| butenes | 0.9% | 1.0% | 0.7% | 1.0% | 2.3% | 1.3% | 1.2% | 1.2% |
| 4-vinyl-1-cyclohexene | 0.0% | 0.0% | 0.0% | 0.0% | 0.0% | 0.0% | 0.0% | 0.0% |
| acetone | 0.0% | 0.0% | 0.0% | 1.9% | 2.3% | 2.1% | 1.9% | 1.7% |
| isobutyraldehyde | 6.8% | 6.9% | 6.5% | 6.2% | 5.7% | 8.4% | 7.4% | 9.0% |
| 2,3-butanedione | 0.0% | 0.0% | 0.0% | 0.0% | 0.0% | 1.8% | 2.1% | 1.9% |
| MEK | 42.4% | 42.0% | 41.6% | 43.7% | 40.6% | 47.1% | 43.9% | 44.2% |
| acetoin | 0.0% | 0.0% | 0.0% | 0.0% | 0.0% | 0.0% | 0.0% | 0.0% |
| MVC | 1.0% | 1.4% | 1.5% | 1.2% | 1.0% | 1.7% | 2.8% | 2.2% |
| isobutanol | 9.0% | 9.2% | 7.6% | 8.7% | 5.1% | 10.2% | 8.7% | 8.5% |
| 2-butanol | 2.0% | 1.9% | 1.4% | 1.9% | 1.3% | 1.9% | 1.7% | 1.3% |
| 2-buteneol | 0.9% | 1.0% | 0.0% | 1.0% | 0.8% | 1.0% | 0.0% | 0.0% |
| unknown | 1.3% | 1.4% | 1.6% | 1.8% | 1.9% | 2.2% | 2.3% | 3.6% |
| Total | 62.5% | 62.9% | 60.1% | 65.2% | 64.5% | 75.4% | 70.0% | 71.9% |

TABLE 16

Screening 3 (cont'd), 400° C., 6 h

| Catalyst: | 3-1 | 3-2 | 3-3 | 3-4 | 3-5 | 3-6 | 3-7 | 3-8 |
|---|---|---|---|---|---|---|---|---|
| BDO Conversion | 100.0% | 100.0% | 100.0% | 99.2% | 100.0% | 100.0% | 100.0% | 100.0% |
| 1,3 butadiene | 2.2% | 2.2% | 2.3% | 2.1% | 3.9% | 2.2% | 1.9% | 3.3% |
| butenes | 1.2% | 1.1% | 0.7% | 1.1% | 1.4% | 1.2% | 1.0% | 1.2% |
| 4-vinyl-1-cyclohexene | 0.0% | 0.0% | 0.0% | 0.0% | 0.0% | 0.0% | 0.0% | 0.0% |
| acetone | 0.8% | 0.8% | 0.6% | 0.9% | 0.9% | 0.9% | 0.7% | 0.6% |
| isobutyraldehyde | 10.9% | 10.9% | 9.7% | 10.6% | 8.3% | 12.2% | 9.9% | 11.1% |
| 2,3-butanedione | 3.0% | 3.2% | 2.5% | 3.3% | 1.7% | 4.3% | 3.4% | 3.1% |
| MEK | 47.4% | 42.7% | 42.9% | 47.1% | 39.2% | 46.2% | 42.3% | 45.5% |
| acetoin | 0.0% | 0.0% | 0.0% | 0.0% | 0.0% | 0.0% | 0.0% | 0.0% |
| MVC | 2.9% | 3.3% | 3.0% | 4.1% | 2.2% | 4.9% | 4.8% | 5.3% |
| isobutanol | 11.4% | 11.3% | 9.9% | 11.7% | 6.5% | 12.3% | 10.8% | 10.4% |
| 2-butanol | 1.6% | 1.6% | 1.4% | 1.7% | 1.2% | 1.6% | 1.7% | 1.1% |
| 2-buteneol | 0.0% | 0.0% | 0.0% | 0.0% | 0.0% | 0.0% | 0.0% | 0.0% |
| unknown | 4.0% | 4.0% | 3.4% | 3.9% | 4.0% | 4.4% | 3.5% | 6.1% |
| Total | 79.8% | 75.6% | 71.6% | 80.8% | 64.1% | 84.2% | 74.9% | 80.5% |

TABLE 17

Screening 4, 350° C., 3 h

| Catalyst: | 4-1 | 4-2 | 4-3 | 4-4 | 4-5 | 4-6 | 4-7 | 4-8 |
|---|---|---|---|---|---|---|---|---|
| BDO Conversion | 72.1% | 82.8% | 82.8% | 89.0% | 87.8% | 23.0% | 33.2% | 49.7% |
| 1,3 butadiene | 0.0% | 0.0% | 0.0% | 0.0% | 0.0% | 0.0% | 0.0% | 0.0% |
| butenes | — | — | — | — | — | — | — | — |
| 4-vinyl-1-cyclohexene | 0.0% | 0.0% | 0.0% | 0.0% | 0.0% | 0.0% | 0.0% | 0.0% |
| acetone | 1.2% | 1.3% | 0.9% | 0.9% | 1.0% | 1.2% | 1.1% | 1.0% |
| isobutyraldehyde | 1.5% | 1.1% | 0.8% | 0.0% | 1.1% | 0.0% | 0.0% | 0.4% |
| 2,3-butanedione | 3.1% | 2.5% | 2.6% | 5.6% | 5.7% | 1.8% | 1.9% | 2.2% |
| MEK | 11.4% | 13.2% | 11.3% | 4.3% | 7.1% | 3.5% | 3.2% | 4.1% |
| acetoin | 13.1% | 8.5% | 8.7% | 5.9% | 27.2% | 2.8% | 4.3% | 7.6% |

TABLE 17-continued

Screening 4, 350° C., 3 h

| Catalyst: | 4-1 | 4-2 | 4-3 | 4-4 | 4-5 | 4-6 | 4-7 | 4-8 |
|---|---|---|---|---|---|---|---|---|
| MVC | 9.2% | 11.2% | 12.7% | 42.6% | 19.5% | 1.2% | 2.0% | 7.3% |
| isobutanol | 11.8% | 11.5% | 9.9% | 0.0% | 2.4% | 0.8% | 0.8% | 2.6% |
| 2-butanol | 1.8% | 2.6% | 2.3% | 0.0% | 0.0% | 0.0% | 1.2% | 2.2% |
| 2-buteneol | 0.0% | 0.0% | 0.0% | 0.0% | 0.0% | 0.0% | 0.0% | 0.0% |
| unknown | — | — | — | — | — | — | — | — |
| Total | 51.3% | 49.3% | 46.8% | 59.3% | 64.1% | 11.3% | 13.3% | 25.2% |

TABLE 18

Screening 4 (cont'd), 350° C., 3 h

| Catalyst: | 4-9 | 4-10 | 4-11 | 4-12 | 4-13 | 4-14 | 4-15 | 4-16 |
|---|---|---|---|---|---|---|---|---|
| BDO Conversion | 100.0% | 39.2% | 32.4% | 34.8% | 34.7% | 16.3% | 62.2% | 31.6% |
| 1,3 butadiene | 0.0% | 0.0% | 0.0% | 0.0% | 0.0% | 0.0% | 0.0% | 0.0% |
| butenes | — | — | — | — | — | — | — | — |
| 4-vinyl-1-cyclohexene | 0.0% | 0.0% | 0.0% | 0.0% | 0.0% | 0.0% | 5.7% | 0.0% |
| acetone | 0.0% | 1.3% | 1.3% | 1.4% | 1.1% | 1.3% | 0.7% | 1.0% |
| isobutyraldehyde | 0.0% | 0.0% | 0.0% | 0.0% | 0.0% | 0.0% | 1.3% | 0.8% |
| 2,3-butanedione | 0.0% | 1.9% | 1.7% | 0.0% | 1.6% | 2.0% | 0.0% | 1.8% |
| MEK | 2.2% | 1.8% | 2.9% | 1.3% | 3.1% | 3.7% | 21.6% | 5.8% |
| acetoin | 0.0% | 4.9% | 1.9% | 5.1% | 0.0% | 0.0% | 0.0% | 0.0% |
| MVC | 0.0% | 0.8% | 0.0% | 1.0% | 1.0% | 1.2% | 0.0% | 1.3% |
| isobutanol | 0.3% | 0.7% | 0.6% | 0.4% | 0.0% | 0.0% | 0.0% | 0.0% |
| 2-butanol | 0.0% | 1.6% | 0.0% | 1.3% | 0.0% | 0.0% | 0.0% | 0.0% |
| 2-buteneol | 0.0% | 0.0% | 0.0% | 0.0% | 0.0% | 0.0% | 0.0% | 0.0% |
| unknown | — | — | — | — | — | — | — | — |
| Total | 2.5% | 11.3% | 8.4% | 9.1% | 6.8% | 8.2% | 29.2% | 10.8% |

TABLE 19

Screening 4 Repeat, 350° C., 3 h

| Catalyst: | 4-1 | 4-2 | 4-3 | 4-4 | 4-5 | 4-6 | 4-7 | 4-8 |
|---|---|---|---|---|---|---|---|---|
| BDO Conversion | 83.9% | 94.9% | 83.4% | 76.7% | 82.5% | 32.5% | 29.3% | 43.2% |
| 1,3 butadiene | 0.0% | 0.0% | 0.0% | 0.0% | 0.0% | 0.0% | 0.0% | 0.0% |
| Butenes | 0.1% | 0.2% | 0.2% | 3.1% | 0.6% | 0.6% | 0.6% | 0.4% |
| 4-vinyl-1-cyclohexene | 0.0% | 0.0% | 0.0% | 0.0% | 0.0% | 0.0% | 0.0% | 0.0% |
| Acetone | 1.7% | 1.9% | 1.3% | 1.4% | 1.5% | 1.5% | 1.6% | 1.6% |
| isobutyraldehyde | 3.3% | 2.4% | 1.0% | 0.0% | 1.3% | 0.0% | 0.0% | 0.6% |
| 2,3-butanedione | 2.2% | 0.0% | 2.3% | 6.3% | 4.8% | 2.0% | 2.1% | 2.3% |
| MEK | 14.0% | 17.6% | 11.1% | 5.5% | 8.0% | 2.9% | 2.9% | 4.0% |
| Acetoin | 11.0% | 2.6% | 6.9% | 5.3% | 24.3% | 2.6% | 4.3% | 7.1% |
| MVC | 6.0% | 6.9% | 9.4% | 29.9% | 14.1% | 1.0% | 1.7% | 5.9% |
| isobutanol | 14.3% | 14.5% | 9.4% | 0.0% | 3.0% | 0.6% | 0.8% | 2.8% |
| 2-butanol | 2.5% | 3.4% | 2.4% | 0.0% | 0.0% | 0.9% | 1.4% | 2.2% |
| 2-buteneol | 0.0% | 0.0% | 0.0% | 0.0% | 0.0% | 0.0% | 0.0% | 0.0% |
| Total | 52.5% | 46.1% | 41.6% | 51.4% | 57.4% | 11.2% | 14.0% | 24.9% |

TABLE 20

Screening 4 Repeat (cont'd), 350° C., 3 h

| Catalyst: | 4-9 | 4-10 | 4-11 | 4-12 | 4-13 | 4-14 | 4-15 | 4-16 |
|---|---|---|---|---|---|---|---|---|
| BDO Conversion | 51.7% | 38.9% | 33.2% | 42.7% | 34.1% | 21.2% | 91.3% | 19.8% |
| 1,3 butadiene | 0.0% | 0.0% | 0.0% | 0.0% | 0.0% | 0.0% | 1.5% | 0.0% |
| Butenes | 0.4% | 0.7% | 0.5% | 0.5% | 0.3% | 0.3% | 0.6% | 1.0% |
| 4-vinyl-1-cyclohexene | 0.0% | 0.0% | 0.0% | 0.0% | 0.0% | 0.0% | 3.9% | 0.0% |
| Acetone | 1.8% | 1.7% | 1.4% | 1.7% | 1.4% | 1.6% | 0.7% | 1.5% |
| isobutyraldehyde | 0.0% | 0.0% | 0.0% | 0.6% | 0.0% | 0.3% | 9.6% | 1.3% |
| 2,3-butanedione | 2.1% | 1.9% | 1.7% | 1.8% | 1.7% | 2.1% | 0.0% | 2.0% |

TABLE 20-continued

Screening 4 Repeat (cont'd), 350° C., 3 h

| Catalyst: | 4-9 | 4-10 | 4-11 | 4-12 | 4-13 | 4-14 | 4-15 | 4-16 |
|---|---|---|---|---|---|---|---|---|
| MEK | 6.5% | 1.7% | 2.7% | 1.7% | 4.2% | 4.0% | 49.8% | 6.6% |
| Acetoin | 4.2% | 4.2% | 1.7% | 4.9% | 0.0% | 0.0% | 0.0% | 0.0% |
| MVC | 3.4% | 0.0% | 0.0% | 0.7% | 1.0% | 1.0% | 0.0% | 1.2% |
| isobutanol | 1.8% | 0.6% | 0.5% | 0.7% | 0.0% | 0.0% | 0.0% | 0.0% |
| 2-butanol | 1.9% | 1.5% | 0.0% | 1.7% | 0.0% | 0.0% | 0.0% | 0.0% |
| 2-buteneol | 0.0% | 0.0% | 0.0% | 0.0% | 0.0% | 0.0% | 0.0% | 0.0% |
| unknown | 0.5% | 0.4% | 0.1% | 0.8% | 0.5% | 0.6% | 5.4% | 1.3% |
| Total | 20.1% | 10.8% | 8.6% | 12.4% | 8.6% | 9.3% | 66.1% | 13.6% |

TABLE 21

Screening 4 Repeat (cont'd), 350° C., 6 h

| Catalyst: | 4-1 | 4-2 | 4-3 | 4-4 | 4-5 | 4-6 | 4-7 | 4-8 |
|---|---|---|---|---|---|---|---|---|
| BDO Conversion | 80.1% | 98.0% | 51.1% | 48.7% | 65.2% | — | 49.8% | 18.3% |
| 1,3 butadiene | 0.3% | 0.2% | 0.3% | 1.2% | 0.4% | 0.1% | 0.3% | 0.1% |
| Butenes | 0.2% | 0.4% | 0.6% | 4.5% | 0.9% | 1.1% | 1.1% | 0.8% |
| 4-vinyl-1-cyclohexene | 0.0% | 0.0% | 0.0% | 0.0% | 0.0% | 0.0% | 0.0% | 0.0% |
| Acetone | 0.0% | 0.0% | 0.0% | 0.0% | 0.0% | 0.0% | 0.0% | 0.0% |
| isobutyraldehyde | 3.5% | 0.0% | 0.5% | 0.0% | 0.6% | 0.0% | 0.3% | 0.0% |
| 2,3-butanedione | 1.8% | 0.0% | 2.4% | 4.5% | 3.7% | 0.0% | 0.0% | 2.0% |
| MEK | 14.5% | 2.1% | 11.4% | 5.1% | 7.6% | 2.3% | 2.2% | 3.6% |
| Acetoin | 9.4% | 0.0% | 10.2% | 10.4% | 27.4% | 1.2% | 2.9% | 6.1% |
| MVC | 4.2% | 0.8% | 11.8% | 22.0% | 14.9% | 0.0% | 0.0% | 3.9% |
| isobutanol | 13.5% | 0.9% | 8.9% | 0.0% | 2.9% | 0.0% | 0.6% | 2.5% |
| 2-butanol | 2.2% | 0.0% | 2.2% | 0.0% | 0.0% | 0.0% | 1.3% | 1.5% |
| 2-buteneol | 0.0% | 0.0% | 0.0% | 0.0% | 0.0% | 0.0% | 0.0% | 0.0% |
| unknown | 1.6% | 0.2% | 0.6% | 0.3% | 0.6% | 0.0% | 0.4% | 0.4% |
| Total | 47.5% | 4.4% | 46.2% | 47.7% | 58.3% | 4.8% | 7.4% | 19.2% |

TABLE 22

Screening 4 Repeat (cont'd), 350° C., 6 h

| Catalyst: | 4-9 | 4-10 | 4-11 | 4-12 | 4-13 | 4-14 | 4-15 | 4-16 |
|---|---|---|---|---|---|---|---|---|
| BDO Conversion | 26.8% | 10.7% | 46.4% | 17.8% | 18.9% | — | 95.5% | — |
| 1,3 butadiene | 0.1% | 0.1% | 0.2% | 0.1% | 0.4% | 0.4% | 14.1% | 2.2% |
| Butenes | 0.7% | 1.2% | 1.0% | 0.9% | 0.4% | 0.5% | 0.6% | 1.0% |
| 4-vinyl-1-cyclohexene | 0.0% | 0.0% | 0.0% | 0.0% | 0.0% | 0.0% | 0.6% | 0.0% |
| Acetone | 0.0% | 0.0% | 0.0% | 0.0% | 0.0% | 0.0% | 0.0% | 0.0% |
| isobutyraldehyde | 0.0% | 0.0% | 0.0% | 0.0% | 0.0% | 0.0% | 12.5% | 0.9% |
| 2,3-butanedione | 1.9% | 0.0% | 0.0% | 0.0% | 0.0% | 1.9% | 0.0% | 2.0% |
| MEK | 5.3% | 1.3% | 2.0% | 1.1% | 4.2% | 3.8% | 73.6% | 7.3% |
| Acetoin | 3.9% | 3.6% | 1.4% | 4.1% | 0.0% | 0.0% | 0.0% | 0.0% |
| MVC | 1.9% | 0.0% | 0.0% | 0.0% | 0.8% | 0.8% | 0.0% | 1.2% |
| isobutanol | 1.3% | 0.4% | 0.0% | 0.4% | 0.0% | 0.0% | 0.0% | 0.0% |
| 2-butanol | 1.7% | 1.2% | 0.0% | 1.4% | 0.0% | 0.0% | 0.0% | 0.0% |
| 2-buteneol | 0.0% | 0.0% | 0.0% | 0.0% | 0.0% | 0.0% | 0.0% | 0.0% |
| unknown | 0.1% | 0.2% | 0.1% | 0.4% | 0.3% | 0.5% | 6.9% | 1.1% |
| Total | 15.1% | 6.5% | 4.6% | 6.6% | 5.7% | 7.4% | 101.4% | 14.7% |

TABLE 23

Screening 5, 350° C., 3 h

| Catalyst: | 5-1 | 5-2 | 5-3 | 5-4 | 5-5 | 5-6 | 5-7 | 5-8 |
|---|---|---|---|---|---|---|---|---|
| BDO Conversion | 84.2% | 39.7% | 41.5% | 19.0% | 41.4% | 26.4% | 24.9% | 14.0% |
| 1,3 butadiene | 0.0% | 0.0% | 0.0% | 0.0% | 0.0% | 0.0% | 0.0% | 0.0% |
| Butenes | 0.1% | 0.3% | 0.3% | 0.1% | 0.2% | 0.3% | 0.3% | 0.2% |
| 4-vinyl-1-cyclohexene | 0.0% | 0.0% | 0.0% | 0.0% | 0.0% | 0.0% | 0.0% | 0.0% |

TABLE 23-continued

Screening 5, 350° C., 3 h

| Catalyst: | 5-1 | 5-2 | 5-3 | 5-4 | 5-5 | 5-6 | 5-7 | 5-8 |
|---|---|---|---|---|---|---|---|---|
| Acetone | 1.9% | 1.8% | 1.5% | 1.9% | 1.6% | 1.9% | 1.8% | 1.8% |
| isobutyraldehyde | 2.6% | 0.0% | 0.0% | 0.0% | 0.0% | 0.0% | 0.0% | 0.0% |
| 2,3-butanedione | 3.3% | 1.7% | 0.0% | 1.9% | 1.9% | 2.0% | 1.8% | 2.0% |
| MEK | 15.5% | 2.9% | 2.9% | 3.4% | 2.5% | 3.1% | 2.6% | 4.3% |
| acetoin | 14.5% | 4.5% | 2.9% | 2.6% | 4.1% | 2.7% | 2.9% | 0.8% |
| MVC | 10.4% | 1.2% | 0.0% | 0.0% | 1.0% | 0.8% | 0.0% | 0.0% |
| isobutanol | 15.1% | 0.8% | 0.6% | 0.7% | 0.7% | 0.7% | 0.6% | 0.0% |
| 2-butanol | 2.3% | 1.3% | 1.0% | 0.0% | 1.1% | 0.0% | 0.9% | 0.0% |
| 2-buteneol | 0.0% | 0.0% | 0.0% | 0.0% | 0.0% | 0.0% | 0.0% | 0.0% |
| unknown | 1.3% | 0.3% | 0.2% | 0.1% | 0.3% | 0.3% | 0.2% | 0.3% |
| Total | 63.3% | 13.3% | 8.2% | 10.7% | 12.0% | 11.4% | 10.0% | 9.1% |

TABLE 24

Screening 5 (cont'd), 350° C., 3 h

| Catalyst: | 5-9 | 5-10 | 65-11 | 5-12 | 5-13 | 5-14 | 5-15 | 5-16 |
|---|---|---|---|---|---|---|---|---|
| BDO Conversion | 15.4% | 22.5% | 34.1% | 73.1% | 43.4% | 76.6% | 42.3% | 45.7% |
| 1,3 butadiene | 0.0% | 0.0% | 0.0% | 0.0% | 0.0% | 4.9% | 0.0% | 0.0% |
| butenes | 0.2% | 0.1% | 0.1% | 0.2% | 0.1% | 14.1% | 0.1% | 0.5% |
| 4-vinyl-1-cyclohexene | 0.0% | 0.0% | 0.0% | 0.0% | 0.0% | 0.0% | 0.0% | 0.0% |
| acetone | 2.3% | 2.0% | 1.7% | 2.2% | 2.4% | 1.9% | 2.0% | 1.6% |
| isobutyraldehyde | 0.0% | 0.0% | 0.0% | 0.7% | 0.0% | 1.2% | 0.0% | 0.0% |
| 2,3-butanedione | 1.9% | 2.0% | 1.9% | 5.9% | 2.5% | 0.0% | 3.2% | 2.8% |
| MEK | 3.0% | 3.9% | 2.8% | 22.8% | 10.1% | 16.9% | 10.3% | 6.2% |
| acetoin | 2.9% | 1.1% | 3.4% | 7.3% | 5.0% | 1.5% | 8.9% | 5.9% |
| MVC | 0.0% | 0.0% | 1.0% | 7.9% | 0.0% | 0.0% | 10.9% | 3.5% |
| isobutanol | 0.6% | 0.4% | 0.7% | 5.1% | 1.5% | 0.0% | 6.1% | 3.8% |
| 2-butanol | 0.0% | 0.0% | 1.0% | 2.0% | 1.4% | 1.1% | 1.1% | 1.0% |
| 2-buteneol | 0.0% | 0.0% | 0.0% | 0.0% | 0.0% | 0.0% | 0.0% | 0.0% |
| unknown | 0.2% | 0.2% | 0.2% | 0.8% | 0.5% | 1.1% | 0.5% | 0.6% |
| Total | 10.8% | 9.6% | 11.7% | 52.2% | 21.7% | 40.6% | 41.5% | 24.3% |

TABLE 25

Screening 5 (cont'd), 350° C., 6 h

| Catalyst: | 5-1 | 5-2 | 5-3 | 5-4 | 5-5 | 5-6 | 5-7 | 5-8 |
|---|---|---|---|---|---|---|---|---|
| BDO Conversion | 70.6% | 27.0% | 23.2% | 3.5% | 18.4% | 34.0% | 9.2% | 1.7% |
| 1,3 butadiene | 0.1% | 0.0% | 0.0% | 0.0% | 0.0% | 0.0% | 0.0% | 0.0% |
| butenes | 0.1% | 0.4% | 0.4% | 0.2% | 0.2% | 0.3% | 0.3% | 0.2% |
| 4-vinyl-1-cyclohexene | 0.0% | 0.0% | 0.0% | 0.0% | 0.0% | 0.0% | 0.0% | 0.0% |
| acetone | 0.0% | 0.0% | 0.0% | 0.0% | 0.0% | 0.0% | 0.0% | 0.0% |
| isobutyraldehyde | 1.8% | 0.0% | 0.0% | 0.0% | 0.0% | 0.0% | 0.0% | 0.0% |
| 2,3-butanedione | 3.7% | 0.0% | 0.0% | 0.0% | 1.8% | 0.0% | 0.0% | 0.0% |
| MEK | 15.3% | 2.4% | 2.7% | 2.7% | 2.2% | 1.7% | 2.0% | 3.4% |
| acetoin | 15.3% | 3.9% | 2.7% | 2.0% | 3.7% | 2.8% | 2.5% | 0.9% |
| MVC | 11.2% | 1.1% | 0.0% | 0.0% | 1.1% | 0.0% | 0.0% | 0.0% |
| isobutanol | 12.9% | 0.4% | 0.0% | 0.0% | 0.0% | 0.4% | 0.0% | 0.0% |
| 2-butanol | 2.0% | 0.9% | 0.8% | 0.0% | 0.0% | 0.9% | 0.0% | 0.0% |
| 2-buteneol | 0.0% | 0.0% | 0.0% | 0.0% | 0.0% | 0.0% | 0.0% | 0.0% |
| unknown | 1.0% | 0.2% | 0.1% | 0.1% | 0.1% | 0.3% | 0.1% | 0.1% |
| Total | 60.4% | 8.2% | 5.8% | 4.9% | 9.0% | 5.3% | 4.9% | 4.6% |

TABLE 26

Screening 5 (cont'd), 350° C., 6 h

| Catalyst: | 5-9 | 5-10 | 65-11 | 5-12 | 5-13 | 5-14 | 5-15 | 5-16 |
|---|---|---|---|---|---|---|---|---|
| BDO Conversion | 2.2% | 5.6% | 22.4% | 57.4% | 40.4% | 35.0% | 31.9% | 31.6% |
| 1,3 butadiene | 0.0% | 0.0% | 0.0% | 0.2% | 0.0% | 3.1% | 0.1% | 0.1% |
| butenes | 0.2% | 0.2% | 0.1% | 0.2% | 0.1% | 7.6% | 0.1% | 0.5% |
| 4-vinyl-1-cyclohexene | 0.0% | 0.0% | 0.0% | 0.0% | 0.0% | 0.0% | 0.0% | 0.0% |
| acetone | 0.0% | 0.0% | 0.0% | 0.0% | 0.0% | 0.0% | 0.0% | 0.0% |
| isobutyraldehyde | 0.0% | 0.0% | 0.0% | 0.4% | 0.0% | 0.4% | 0.0% | 0.0% |
| 2,3-butanedione | 0.0% | 0.0% | 0.0% | 7.3% | 2.2% | 0.0% | 3.0% | 2.8% |
| MEK | 2.3% | 3.3% | 2.3% | 22.5% | 10.4% | 12.7% | 10.6% | 6.1% |
| acetoin | 2.4% | 1.0% | 2.7% | 6.4% | 5.1% | 1.5% | 8.5% | 5.4% |
| MVC | 0.0% | 0.0% | 0.9% | 6.7% | 0.0% | 0.0% | 11.7% | 3.7% |
| isobutanol | 0.0% | 0.0% | 0.4% | 3.9% | 1.0% | 0.0% | 5.4% | 3.1% |
| 2-butanol | 0.0% | 0.0% | 0.0% | 1.5% | 1.4% | 0.0% | 0.9% | 0.0% |
| 2-buteneol | 0.0% | 0.0% | 0.0% | 0.0% | 0.0% | 0.0% | 0.0% | 0.0% |
| unknown | 0.1% | 0.1% | 0.1% | 0.6% | 0.4% | 0.7% | 0.4% | 0.4% |
| Total | 5.0% | 4.4% | 6.4% | 47.6% | 18.8% | 25.4% | 39.3% | 21.6% |

TABLE 27

Screening 6, 350° C., 3 h

| Catalyst: | 6-1 | 6-2 | 6-3 | 6-4 | 6-5 | 6-6 | 6-7 | 6-8 |
|---|---|---|---|---|---|---|---|---|
| BDO Conversion | 80.0% | 100.0% | 55.7% | 100.0% | 70.3% | 67.1% | 69.4% | 75.9% |
| 1,3 butadiene | 0.0% | 0.0% | 0.0% | 0.0% | 0.0% | 0.0% | 0.0% | 0.0% |
| butenes | 0.1% | 0.3% | 0.2% | 4.0% | 0.2% | 0.2% | 0.1% | 0.1% |
| 4-vinyl-1-cyclohexene | 0.0% | 0.0% | 0.0% | 0.0% | 0.0% | 0.0% | 0.0% | 0.0% |
| acetone | 0.0% | 0.0% | 0.0% | 0.0% | 0.0% | 0.0% | 0.0% | 0.0% |
| isobutyraldehyde | 1.4% | 2.8% | 0.0% | 12.9% | 0.0% | 3.6% | 0.7% | 2.0% |
| 2,3-butanedione | 3.2% | 0.0% | 1.8% | 2.9% | 2.1% | 3.4% | 2.7% | 4.1% |
| MEK | 12.7% | 31.5% | 5.0% | 34.6% | 5.3% | 16.0% | 8.9% | 16.9% |
| acetoin | 14.4% | 1.6% | 4.0% | 1.7% | 6.8% | 13.3% | 12.0% | 18.3% |
| MVC | 10.9% | 4.2% | 7.3% | 0.0% | 5.1% | 7.4% | 7.5% | 13.2% |
| isobutanol | 13.4% | 7.1% | 3.0% | 8.3% | 5.1% | 11.9% | 10.3% | 17.8% |
| 2-butanol | 2.0% | 2.2% | 0.0% | 0.0% | 1.4% | 0.0% | 2.5% | 2.7% |
| 2-buteneol | 0.0% | 0.0% | 0.0% | 0.0% | 0.0% | 0.0% | 0.0% | 0.0% |
| unknown | 1.9% | 2.5% | 0.4% | 9.7% | 1.2% | 3.1% | 1.4% | 2.2% |
| Total | 56.2% | 47.4% | 21.2% | 64.4% | 24.5% | 55.8% | 42.3% | 72.3% |

TABLE 28

Screening 6 (cont'd), 350° C., 3 h

| Catalyst: | 6-9 | 6-10 | 6-11 | 6-12 | 6-13 | 6-14 | 6-15 | 6-16 |
|---|---|---|---|---|---|---|---|---|
| BDO Conversion | 27.1% | 40.9% | 88.7% | 8.1% | 25.7% | 16.9% | 25.3% | 19.5% |
| 1,3 butadiene | 0.0% | 0.0% | 0.0% | 0.0% | 0.0% | 0.0% | 0.0% | 0.0% |
| butenes | 0.1% | 0.1% | 0.3% | 0.1% | 0.1% | 0.1% | 0.1% | 0.1% |
| 4-vinyl-1-cyclohexene | 0.0% | 0.0% | 0.0% | 0.0% | 0.0% | 0.0% | 0.0% | 0.0% |
| acetone | 0.0% | 0.0% | 0.0% | 0.0% | 0.0% | 0.0% | 0.0% | 0.0% |
| isobutyraldehyde | 0.0% | 0.9% | 0.0% | 0.0% | 0.0% | 0.0% | 0.0% | 0.0% |
| 2,3-butanedione | 2.7% | 2.8% | 0.0% | 0.0% | 0.0% | 2.0% | 0.0% | 1.9% |
| MEK | 3.4% | 8.6% | 2.6% | 2.9% | 2.8% | 3.7% | 3.9% | 3.5% |
| acetoin | 3.9% | 6.7% | 2.5% | 2.7% | 2.7% | 2.9% | 2.5% | 2.3% |
| MVC | 4.4% | 10.4% | 4.1% | 0.0% | 0.9% | 5.1% | 4.7% | 7.5% |
| isobutanol | 1.8% | 5.5% | 0.0% | 0.8% | 0.9% | 1.6% | 1.4% | 1.2% |
| 2-butanol | 0.0% | 0.0% | 0.0% | 0.0% | 0.0% | 0.0% | 0.0% | 0.0% |
| 2-buteneol | 0.0% | 0.0% | 0.0% | 0.0% | 0.0% | 0.0% | 0.0% | 0.0% |
| unknown | 0.4% | 1.5% | 0.2% | 0.1% | 0.2% | 0.5% | 0.5% | 0.4% |
| Total | 16.3% | 35.1% | 9.5% | 6.6% | 7.4% | 15.5% | 12.6% | 16.4% |

TABLE 29

Screening 6 (cont'd), 350° C., 6 h

| Catalyst: | 6-1 | 6-2 | 6-3 | 6-4 | 6-5 | 6-6 | 6-7 | 6-8 |
|---|---|---|---|---|---|---|---|---|
| BDO Conversion | 64.0% | 100.0% | 39.7% | 66.3% | 53.5% | 50.9% | 55.3% | 62.6% |
| 1,3 butadiene | 0.1% | 2.0% | 0.1% | 0.6% | 0.1% | 0.2% | 0.1% | 0.1% |
| butenes | 0.1% | 0.3% | 0.2% | 0.8% | 0.1% | 0.2% | 0.1% | 0.1% |
| 4-vinyl-1-cyclohexene | 0.0% | 0.0% | 0.0% | 0.0% | 0.0% | 0.0% | 0.0% | 0.0% |
| acetone | 0.0% | 0.0% | 0.0% | 0.0% | 0.0% | 0.0% | 0.0% | 0.0% |
| isobutyraldehyde | 1.0% | 3.0% | 0.0% | 9.0% | 0.0% | 2.7% | 0.4% | 1.3% |
| 2,3-butanedione | 3.8% | 1.9% | 0.0% | 2.9% | 2.4% | 3.6% | 2.8% | 4.1% |
| MEK | 15.8% | 44.2% | 6.1% | 28.3% | 6.7% | 17.5% | 10.9% | 18.2% |
| acetoin | 15.8% | 4.4% | 3.8% | 7.0% | 7.1% | 12.0% | 12.5% | 17.2% |
| MVC | 13.0% | 6.3% | 8.0% | 2.8% | 5.9% | 7.8% | 8.3% | 13.5% |
| isobutanol | 12.4% | 7.2% | 2.7% | 6.8% | 4.4% | 9.6% | 9.2% | 13.9% |
| 2-butanol | 1.7% | 1.9% | 0.0% | 0.0% | 1.2% | 0.0% | 2.2% | 2.0% |
| 2-buteneol | 0.0% | 0.0% | 0.0% | 0.0% | 0.0% | 0.0% | 0.0% | 0.0% |
| unknown | 1.4% | 3.0% | 0.3% | 7.6% | 0.7% | 2.7% | 1.0% | 1.7% |
| Total | 61.9% | 69.1% | 20.9% | 58.1% | 26.8% | 53.5% | 44.4% | 68.4% |

TABLE 30

Screening 6 (cont'd), 350° C., 6 h

| Catalyst: | 6-9 | 6-10 | 6-11 | 6-12 | 6-13 | 6-14 | 6-15 | 6-16 |
|---|---|---|---|---|---|---|---|---|
| BDO Conversion | 9.1% | 34.1% | 80.2% | - | 17.0% | 8.4% | 10.1% | 9.1% |
| 1,3 butadiene | 0.0% | 0.1% | 0.0% | 0.0% | 0.0% | 0.0% | 0.2% | 0.0% |
| butenes | 0.1% | 0.1% | 0.3% | 0.1% | 0.1% | 0.1% | 0.1% | 0.1% |
| 4-vinyl-1-cyclohexene | 0.0% | 0.0% | 0.0% | 0.0% | 0.0% | 0.0% | 0.0% | 0.0% |
| acetone | 0.0% | 0.0% | 0.0% | 0.0% | 0.0% | 0.0% | 0.0% | 0.0% |
| isobutyraldehyde | 0.0% | 0.9% | 0.0% | 0.0% | 0.0% | 0.0% | 0.0% | 0.0% |
| 2,3-butanedione | 2.7% | 2.7% | 0.0% | 0.0% | 0.0% | 0.0% | 0.0% | 0.0% |
| MEK | 3.9% | 10.1% | 2.9% | 2.7% | 2.6% | 3.9% | 4.5% | 3.8% |
| acetoin | 3.6% | 6.4% | 3.0% | 2.1% | 2.4% | 2.4% | 2.2% | 1.8% |
| MVC | 4.9% | 11.2% | 3.3% | 0.0% | 1.0% | 5.4% | 5.5% | 7.9% |
| isobutanol | 1.5% | 5.0% | 0.0% | 0.4% | 0.5% | 1.2% | 1.0% | 0.8% |
| 2-butanol | 0.0% | 0.0% | 0.0% | 0.0% | 0.0% | 0.0% | 0.0% | 0.0% |
| 2-buteneol | 0.0% | 0.0% | 0.0% | 0.0% | 0.0% | 0.0% | 0.0% | 0.0% |
| unknown | 0.2% | 1.4% | 0.1% | 0.1% | 0.1% | 0.4% | 0.4% | 0.3% |
| Total | 16.9% | 36.5% | 9.5% | 5.3% | 6.4% | 13.0% | 13.4% | 14.4% |

TABLE 31

Screening 7, 300° C., 3 h

| Catalyst: | 7-1 | 7-2 | 7-4 | 7-7 | 7-8 |
|---|---|---|---|---|---|
| MVC Conversion | 16.4% | 73.8% | 62.2% | 98.4% | 51.3% |
| 1,3 butadiene | 6.6% | 17.7% | 25.9% | 65.6% | 56.6% |
| butenes | 0.0% | 0.1% | 0.1% | 0.9% | 0.4% |
| 4-vinyl-1-cyclohexene | 0.0% | 0.3% | 0.4% | 0.0% | 0.0% |
| acetone | 0.0% | 0.0% | 0.0% | 0.0% | 0.0% |
| isobutyraldehyde | 0.0% | 0.0% | 0.0% | 0.0% | 0.0% |
| 2,3-butanedione | 0.0% | 0.0% | 0.0% | 0.0% | 0.0% |
| MEK | 0.0% | 0.0% | 0.0% | 0.0% | 0.0% |
| acetoin | 0.0% | 0.0% | 0.0% | 0.0% | 0.0% |
| isobutanol | 0.0% | 0.0% | 0.0% | 0.0% | 0.0% |
| 2-butanol | 1.2% | 0.6% | 0.8% | 0.0% | 1.4% |
| 2-buteneol | 3.6% | 1.4% | 1.3% | 0.0% | 4.2% |
| unknown | 0.0% | 0.0% | 0.0% | 0.0% | 0.1% |
| Total | 6.6% | 18.2% | 26.3% | 66.6% | 57.0% |

TABLE 32

Screening 7 (cont'd), 300° C., 3 h

| Catalyst: | 7-11 | 7-12 | 7-13 | 7-14 | 7-15 | 7-16 |
|---|---|---|---|---|---|---|
| MVC Conversion | 100.0% | 75.3% | 100.0% | 67.7% | 100.0% | 100.0% |
| 1,3 butadiene | 3.9% | 69.5% | 118.0% | 46.4% | 59.8% | 16.3% |
| butenes | 148.9% | 1.1% | 2.6% | 0.8% | 2.5% | 0.8% |
| 4-vinyl-1-cyclohexene | 0.0% | 0.0% | 0.0% | 0.0% | 0.0% | 0.0% |
| acetone | 0.0% | 0.0% | 0.0% | 0.0% | 0.0% | 0.0% |
| isobutyraldehyde | 0.0% | 0.0% | 0.0% | 0.0% | 0.0% | 0.0% |
| 2,3-butanedione | 0.0% | 0.0% | 0.0% | 0.0% | 0.0% | 0.0% |
| MEK | 0.8% | 0.7% | 0.6% | 0.6% | 3.7% | 1.0% |
| acetoin | 0.0% | 0.0% | 0.0% | 0.0% | 0.0% | 0.0% |
| isobutanol | 0.0% | 0.0% | 0.0% | 0.0% | 0.0% | 0.0% |
| 2-butanol | 0.0% | 0.7% | 0.0% | 0.7% | 0.0% | 0.0% |
| 2-buteneol | 0.0% | 1.7% | 0.0% | 1.7% | 0.0% | 0.0% |
| unknown | 0.1% | 0.1% | 0.1% | 0.1% | 0.4% | 0.0% |
| Total | 153.5% | 71.4% | 121.3% | 47.9% | 65.9% | 18.2% |

TABLE 33

Screening 7 (cont'd), 400° C., 3 h

| Catalyst: | 7-1 | 7-2 | 7-4 | 7-7 | 7-8 |
|---|---|---|---|---|---|
| MVC Conversion | 26.9% | 81.8% | 67.8% | 100.0% | 46.0% |
| 1,3 butadiene | 19.0% | 17.4% | 46.7% | 55.7% | 116.0% |
| butenes | 0.4% | 0.9% | 1.6% | 2.1% | 2.8% |
| 4-vinyl-1-cyclohexene | 0.0% | 0.0% | 0.0% | 0.0% | 0.0% |
| acetone | 0.0% | 0.0% | 0.0% | 0.0% | 0.0% |
| isobutyraldehyde | 0.0% | 0.0% | 0.0% | 0.0% | 0.0% |
| 2,3-butanedione | 0.0% | 0.0% | 0.0% | 0.0% | 0.0% |
| MEK | 0.0% | 0.0% | 0.0% | 0.0% | 0.7% |
| acetoin | 0.0% | 0.0% | 0.0% | 0.0% | 0.0% |
| isobutanol | 0.0% | 0.0% | 0.0% | 0.0% | 0.0% |
| 2-butanol | 1.0% | 0.0% | 0.6% | 0.0% | 1.1% |
| 2-buteneol | 0.7% | 0.0% | 0.0% | 0.0% | 1.7% |
| unknown | 0.0% | 0.0% | 0.0% | 0.0% | 0.0% |
| Total | 19.4% | 18.4% | 48.2% | 57.8% | 119.4% |

TABLE 34

Screening 7 (cont'd), 400° C., 3 h

| Catalyst: | 7-11 | 7-12 | 7-13 | 7-14 | 7-15 | 7-16 |
|---|---|---|---|---|---|---|
| MVC Conversion | 100.0% | 41.3% | 100.0% | 36.3% | 100.0% | 100.0% |
| 1,3 butadiene | 116.2% | 72.2% | 99.0% | 32.2% | 72.4% | 13.4% |
| butenes | 6.7% | 1.7% | 7.0% | 1.0% | 3.3% | 1.2% |
| 4-vinyl-1-cyclohexene | 0.0% | 0.0% | 0.0% | 0.0% | 0.0% | 0.0% |
| acetone | 0.0% | 0.0% | 0.0% | 0.0% | 0.0% | 0.0% |
| isobutyraldehyde | 0.0% | 0.0% | 0.0% | 0.0% | 0.0% | 0.0% |
| 2,3-butanedione | 0.0% | 0.0% | 0.0% | 0.0% | 0.0% | 0.0% |
| MEK | 0.7% | 0.0% | 0.6% | 0.0% | 1.4% | 0.0% |
| acetoin | 0.0% | 0.0% | 0.0% | 0.0% | 0.0% | 0.0% |
| isobutanol | 0.0% | 0.0% | 0.0% | 0.0% | 0.0% | 0.0% |
| 2-butanol | 0.0% | 1.2% | 0.0% | 1.1% | 0.0% | 0.0% |
| 2-buteneol | 0.0% | 1.5% | 0.0% | 1.1% | 0.0% | 0.0% |
| unknown | 0.1% | 0.0% | 0.1% | 0.0% | 0.1% | 0.0% |
| Total | 123.6% | 73.9% | 106.5% | 33.2% | 77.1% | 14.6% |

Example 3

Flow Reactor Evaluation of Catalysts

A small, continuous fixed bed flow reactor (FIG. 1) was constructed to investigate chemical conversions on a scale larger than those in the pyroprobe and high throughput tests with control of feed rates, temperatures, and pressures. An Isco high-pressure syringe pump 20 (Teledyne Isco, Lincoln, Nebr.) was used to deliver neat or aqueous BDO 10 through a preheater 30 to a ⅜" outer diameter stainless steel reactor tube 40. The tube 40 was packed with 0.5-3.5 g catalyst with glass beads above the bed for feed preheating. When about 0.5 g catalyst was used, the catalyst bed volume was about 0.6 cc with a bed length of about 0.5" (1.3 cm). $In_2O_3$, La-doped $ZrO_2$ (XZ0945/03), and mixed Al/La/Zr oxide (FZO2089) catalysts were evaluated. For this example, the $In_2O_3$ catalyst, from the oxalic acid preparation, was prepared by oxalate decomposition, and calcined at 550° C. for 6 h in air prior to loading. Thermocouples 35, 45 were positioned to measure the temperature of the vapor space and the catalyst bottom, respectively. The liquid feed flow rate was 0.05 mL/min and an inert carrier gas ($N_2$ or Ar) 50 was delivered at 39 cc/min. using a mass flow controller 60. The reactor pressure was nominally 1 atm absolute. A product trap 70 and flow meter 80 were positioned downstream from the reactor tube 40. Testing was varied between 225° C. and 425° C. All samples were collected and analyzed as in Example 2 except that gas samples were withdrawn 75 and injected manually.

Results are shown in Table 35. The $In_2O_3$ catalyst was more selective for MVC than the Brønsted-acidic catalysts tested. MEK selectivity was generally much lower than with the other catalysts.

TABLE 35

Conversion of BDO (near except where noted) in a Flow Reactor

| Run | [4]Cat. | Cat. Mass g | MHSV g BDO/ g · cat/hr | Gas Flow mL/ min | W/F (g · cat)- hr/total mol | T ° C. | [3]BDO Conv. % | BD Yield % | BD Sel % | MVC Yield % | MVC Sel % | MEK Yield % | MEK Sel % | Acetoin Yield % | Acetoin Sel % | Mass Bal % | C Bal % |
|---|---|---|---|---|---|---|---|---|---|---|---|---|---|---|---|---|---|
| [1]11 | FZO 2089 | 3.47 | 0.07 | 9.5 | 66.0 | 250 | 100 | 6 | 8 | 0 | 0 | 94 | 94 | — | — | 100 | — |
|  |  |  |  |  |  | 300 | 100 | 11 | 15 | 0 | 0 | 89 | 89 | — | — | 96 | — |
| [1]13 | FZO 2089 | 3.47 | 0.07 | 9.5 | 66.0 | 350 | 100 | 24 | 24 | 0 | 0 | 72 | 72 | — | — | 101 | 87 |
|  |  |  |  |  |  | 400 | 100 | 9 | 9 | 0 | 0 | 19 | 19 | — | — | 97 | 32 |
|  |  |  |  |  |  | 300 | 100 | 7 | 7 | 0 | 0 | 84 | 84 | — | — | 97 | 97 |
| [2]17 | FZO 2089 | 3.51 | 0.62 | 9.8 | 1.5 | 250 | — | 0.4 | — | — | — | — | — | — | — | — | 98 | — |
|  |  |  |  |  |  | 300 | — | 5.4 | — | — | — | — | — | — | — | — | 95 | — |
|  |  |  |  |  |  | 350 | — | 7.7 | — | — | — | — | — | — | — | — | 97 | — |
|  |  |  |  |  |  | 400 | — | 6.8 | — | — | — | — | — | — | — | — | 104 | — |
|  |  |  |  |  |  | 300 | — | 4.8 | — | — | — | — | — | — | — | — | 100 | — |
| 21 | FZO 2089 | 3.51 | 0.86 | 10 | 60.1 | 350 | — | 2.3 | — | — | — | — | — | — | — | — | 74 | — |
|  |  |  |  | 20 | 42.2 |  | — | 2.6 | — | — | — | — | — | — | — | — | 84 | — |
|  |  |  |  | 30 | 32.5 |  | — | 2.6 | — | — | — | — | — | — | — | — | 79 | — |
| 24 | FZO 2089 | 0.52 | 5.77 | 100 | 1.9 | 350 | 68 | 1.4 | 2.1 | 0 | 0 | 38.7 | 56.9 | 9.7 | 14.3 | 89 | 98 |
|  |  |  |  | 30 | 4.8 |  | 79 | 1.9 | 2.4 | 2.4 | 3.0 | 29.7 | 37.6 | 8.4 | 10.6 | 99 | 77 |
|  |  |  |  | 10 | 9.0 |  | 97 | 1.1 | 1.1 | 0 | 0 | 8.7 | 9.0 | 2.1 | 2.2 | 97 | 18 |
| 27 | XZ0 945/03 | 0.5 | 6.00 | 100 | 1.8 | 300 | 4 | 0 | 0.0 | 3.5 | 87.5 | 3.7 | 92.5 | 3.2 | 80.0 | 103 | 108 |
|  |  |  |  | 100 | 1.8 | 350 | 91 | 0 | 0.0 | 12.9 | 14.2 | 20.8 | 22.9 | 8.2 | 9.0 | 94 | 65 |
|  |  |  |  | 30 | 4.6 | 350 | 90 | 0 | 0.0 | 12.7 | 14.1 | 23.4 | 26.0 | 10.5 | 11.7 | 98 | 74 |

TABLE 35-continued

Conversion of BDO (near except where noted) in a Flow Reactor

| Run | [4]Cat. | Cat. Mass g | MHSV g BDO/ g · cat/hr | Gas Flow mL/ min | W/F (g · cat)- hr/total mol | T ° C. | [3]BDO Conv. % | BD Yield % | BD Sel % | MVC Yield % | MVC Sel % | MEK Yield % | MEK Sel % | Acetoin Yield % | Acetoin Sel % | Mass Bal % | C Bal % |
|---|---|---|---|---|---|---|---|---|---|---|---|---|---|---|---|---|---|
| 29 | XZ0 945/03 | 0.5 | 6.00 | 30 | 4.6 | 350 | 93 | 0 | 0.0 | 13 | 14.0 | 29.2 | 31.4 | 11.6 | 12.5 | 96 | 85 |
| | | | | | | 400 | 100 | 5.9 | 5.9 | 1.5 | 1.5 | 46 | 46.0 | 0 | 0 | 96 | 80 |
| | | | | | | 425 | 100 | 7.9 | 7.9 | 0 | 0 | 42.9 | 42.9 | 0 | 0 | 96 | 78 |
| [2]32 | XZ0 945/03 | 0.5 | 0.30 | 30 | 2.1 | 350 | 100 | 2 | 2 | 6 | 6 | 93 | 93 | 0 | 0 | 99 | — |
| | | | | | | 400 | 100 | 16.2 | 16.2 | 0 | 0 | 58.4 | 58.4 | 0 | 0 | 99 | 93 |
| | | | | | | 425 | 100 | 11.3 | 11.3 | 0 | 0 | 45.7 | 45.7 | 0 | 0 | 97 | 70 |
| 35 | XZ0 945/03 | 0.5 | 6.00 | 30 | 4.6 | 350 | 95 | 0 | 0 | 7.9 | 8.3 | 29.2 | 30.7 | 11 | 11.6 | 97 | 79 |
| | | | | | | 400 | 100 | 1.8 | 1.8 | 1.3 | 1.3 | 42.9 | 42.9 | 0 | 0 | 97 | 73 |
| | | | | | | 425 | 100 | 3.0 | 3.0 | 0 | 0 | 47.2 | 47.2 | 0 | 0 | 96 | 77 |
| 39 | $In_2O_3$ | 0.5 | 6.00 | 30 | 4.6 | 350 | 92 | 2.9 | 3.2 | 41.4 | 45.0 | 6.6 | 7.2 | 6.3 | 6.8 | 98 | 82 |
| | | | | | | 400 | 100 | 1.1 | 1.1 | 8.4 | 8.4 | 28.1 | 28.1 | 7.5 | 7.5 | 100 | 79 |
| | | | | | | 425 | 100 | 0.7 | 0.7 | 4.6 | 4.6 | 32.8 | 32.8 | 7.4 | 7.4 | 100 | 83 |
| [2]42 | $In_2O_3$ | 0.5 | 0.30 | 30 | 2.1 | 350 | 94 | 0 | 0 | 8.7 | 9.3 | 20.2 | 21.5 | 20.2 | 21.5 | 99 | 65 |
| | | | | | | 400 | 100 | 0 | 0 | 5.6 | 5.6 | 29 | 29.0 | 0 | 0 | 99 | 64 |
| | | | | | | 425 | 100 | 0 | 0 | 6.2 | 6.2 | 18.7 | 18.7 | 0 | 0 | 102 | 42 |
| 45 | $In_2O_3$ | 0.5 | 6.00 | 39 | 3.8 | 300 | 56 | 0 | 0 | 36.9 | 65.9 | 1.1 | 2.0 | 11.1 | 19.8 | 98 | 94 |
| | | | | | | 315 | 80 | 0.4 | 0.5 | 47.2 | 59.0 | 2.4 | 3.0 | 9.6 | 12.0 | 87 | 84 |
| | | | | | | 330 | 93 | 1.5 | 1.6 | 50.8 | 54.6 | 4.7 | 5.1 | 5.8 | 6.2 | 101 | 81 |
| | | | | | | 350 | 98 | 4 | 4.1 | 39.6 | 40.4 | 7.8 | 8.0 | 0.8 | 0.8 | 98 | 70 |
| 48 | $In_2O_3$ | 0.5 | 6.12 | 30 | 4.6 | 225 | 0 | 0 | 0 | 0 | 0 | 0 | 0 | 0 | 0 | 97 | 100 |
| | | | | | | 250 | 3.9 | 0 | 0 | 2.8 | 71.8 | 0 | 0 | 1.1 | 28.2 | 98 | 105 |
| | | | | | | 275 | 20 | 0 | 0 | 12.6 | 63.0 | 0 | 0 | 5.3 | 26.5 | 98 | 98 |
| | | | | | | 300 | 49 | 0 | 0 | 32.7 | 66.7 | 0.9 | 1.8 | 11.9 | 24.3 | 101 | 98 |
| [2]55 | $In_2O_3$ | 0.51 | 0.30 | 30.5 | 2.2 | 250 | 11 | 0 | 0 | 3.5 | 31.8 | 0 | 0 | 5.4 | 49.1 | 100 | 100 |
| | | | | | | 300 | 85 | 0 | 0 | 15.1 | 17.8 | 2.2 | 2.6 | 10.4 | 12.2 | 95 | 48 |
| | | | | | | 350 | 97 | 5.2 | 5.4 | 9.1 | 9.4 | 6.5 | 6.7 | 0 | 0 | 86 | 46 |
| 57 | $In_2O_3$ | 0.51 | 6.00 | 32.3 | 4.5 | 250 | 2.2 | 0 | 0 | 0 | 0 | 0 | 0 | 1.9 | 86.4 | 104 | 109 |
| | | | | | | 300 | 39 | 0.4 | 1.0 | 20 | 51.3 | 1.3 | 3.3 | 14.4 | 36.9 | 100 | 100 |
| | | | | | | 350 | 89 | 1.8 | 2.0 | 37 | 41.6 | 7.2 | 8.1 | 10 | 11.2 | 97 | 88 |
| 60 | $In_2O_3$ | 0.5 | 6.02 | 31.6 | 4.5 | 250 | 2 | 0 | 0 | 0.3 | 15.0 | 0 | 0 | 1.3 | 65.0 | 100 | 100 |
| | | | | | | 250 | 3 | 0 | 0 | 2.0 | 66.7 | 0 | 0 | 1 | 33 | 100 | — |
| | | | | | | 300 | 59 | 0.4 | 0.7 | 41.3 | 70.0 | 1.7 | 2.9 | 9.7 | 16.4 | 98 | 100 |
| | | | | | | 350 | 92 | 3.2 | 3.5 | 39.6 | 43.0 | 9 | 9.8 | 8.4 | 9.1 | 96 | 93 |
| 63 | $In_2O_3$ | 0.5 | 6.12 | 29.7 | 4.6 | 250 | 10 | 0.0 | 0.0 | 1.8 | 18.0 | 0.0 | 0.0 | 2.1 | 21.0 | 97 | 95 |
| | | | | | | 300 | 59 | 0.0 | 0.0 | 26.2 | 44.4 | 2.2 | 3.7 | 12.1 | 20.5 | 98 | 87 |
| | | | | | | 350 | 97 | 0.0 | 0.0 | 36.5 | 37.6 | 10.0 | 10.3 | 3.1 | 3.2 | 93 | 75 |
| 66 | $Ga_2O_3$ | 0.5 | 6.12 | 32.1 | 4.4 | 250 | 46 | 0.0 | 0.0 | 1.8 | 3.9 | 11.4 | 24.8 | 1.0 | 2.2 | 99 | 71 |
| | | | | | | 300 | 100 | 12.5 | 12.5 | 0.0 | 0.0 | 65.8 | 65.8 | 0.5 | 0.5 | 100 | 95 |
| | | | | | | 350 | 100 | 7.1 | 7.1 | 0.0 | 0.0 | 63.5 | 63.5 | 0.5 | 0.5 | 96 | 94 |
| 69 | 10% $In_2O_3$/ Silica | 0.5 | 6.00 | 31 | 4.5 | 250 | 13 | 0.0 | 0.0 | 0.0 | 0.0 | 0.1 | 0.8 | 0.3 | 2.3 | 100 | 90 |
| | | | | | | 300 | 16 | 0.0 | 0.0 | 0.9 | 5.6 | 0.7 | 4.4 | 2.6 | 16.3 | 101 | 91 |
| | | | | | | 350 | 45 | 0.0 | 0.0 | 4.0 | 8.9 | 5.2 | 11.6 | 18.8 | 41.8 | 98 | 89 |
| 75 | 10% $SnO_2$/ $In_2O_3$ | 0.5 | 6.24 | 30.2 | 4.6 | 250 | 11 | 0.0 | 0.0 | 1.1 | 10.0 | 0.0 | 0.0 | 0.5 | 4.5 | 100 | 92 |
| | | | | | | 300 | 34 | 0.0 | 0.0 | 14.4 | 42.4 | 0.5 | 1.5 | 4.3 | 12.6 | 96 | 87 |
| | | | | | | 350 | 42 | 0.0 | 0.0 | 11.8 | 28.1 | 2.9 | 6.9 | 11.2 | 26.7 | 96 | 90 |
| 80 | 10% $In_2O_3$/ Hyperion | 0.5 | 6.00 | 30.7 | 4.6 | 250 | 15 | 0.0 | 0.0 | 0.0 | 0.0 | 0.0 | 0.0 | 4.1 | 27.3 | 99 | 90 |
| | | | | | | 300 | 26 | 0.0 | 0.0 | 2.6 | 10.0 | 2.1 | 8.1 | 17.4 | 66.9 | 101 | 101 |
| | | | | | | 350 | 80 | 0.0 | 0.0 | 12.8 | 16.0 | 11.1 | 13.9 | 37.3 | 46.6 | 98 | 100 |
| 83 | MEL 0802/ 03 | 0.52 | 5.88 | 32.9 | 4.5 | 250 | 4 | 0.0 | 0.0 | 0.0 | 0.0 | 0.0 | 0.0 | 0.8 | 20.0 | 106 | 97 |
| | | | | | | 300 | 20 | 0.0 | 0.0 | 1.4 | 7.0 | 1.6 | 8.0 | 2.7 | 13.5 | 98 | 86 |
| | | | | | | 350 | 71 | 0.0 | 0.0 | 12.1 | 17.0 | 21.9 | 30.8 | 16.8 | 23.7 | 99 | 99 |
| 85 | MEL XZ0 945/03 | 0.5 | 6.06 | 32.6 | 4.4 | 250 | 10 | 0.0 | 0.0 | 0.0 | 0.0 | 0.0 | 0.0 | 1.0 | 10.0 | 100 | 91 |
| | | | | | | 300 | 19 | 0.0 | 0.0 | 2.9 | 15.3 | 3.1 | 16.3 | 4.4 | 23.2 | 96 | 93 |
| | | | | | | 350 | 98 | 0.0 | 0.0 | 14.1 | 14.4 | 27.1 | 27.7 | 19.5 | 19.9 | 96 | 106 |

[1]0.1 mL/min dodecane co-fed
[2]5 wt % BDO water
[3]Products were collected in diglyme for Runs 24 to 85
[4]$In_2O_3$ by oxalic acid precipitation method Example 4

Flow Reactor Evaluation of Al/La/Zr Oxide Catalyst

Figure 2:
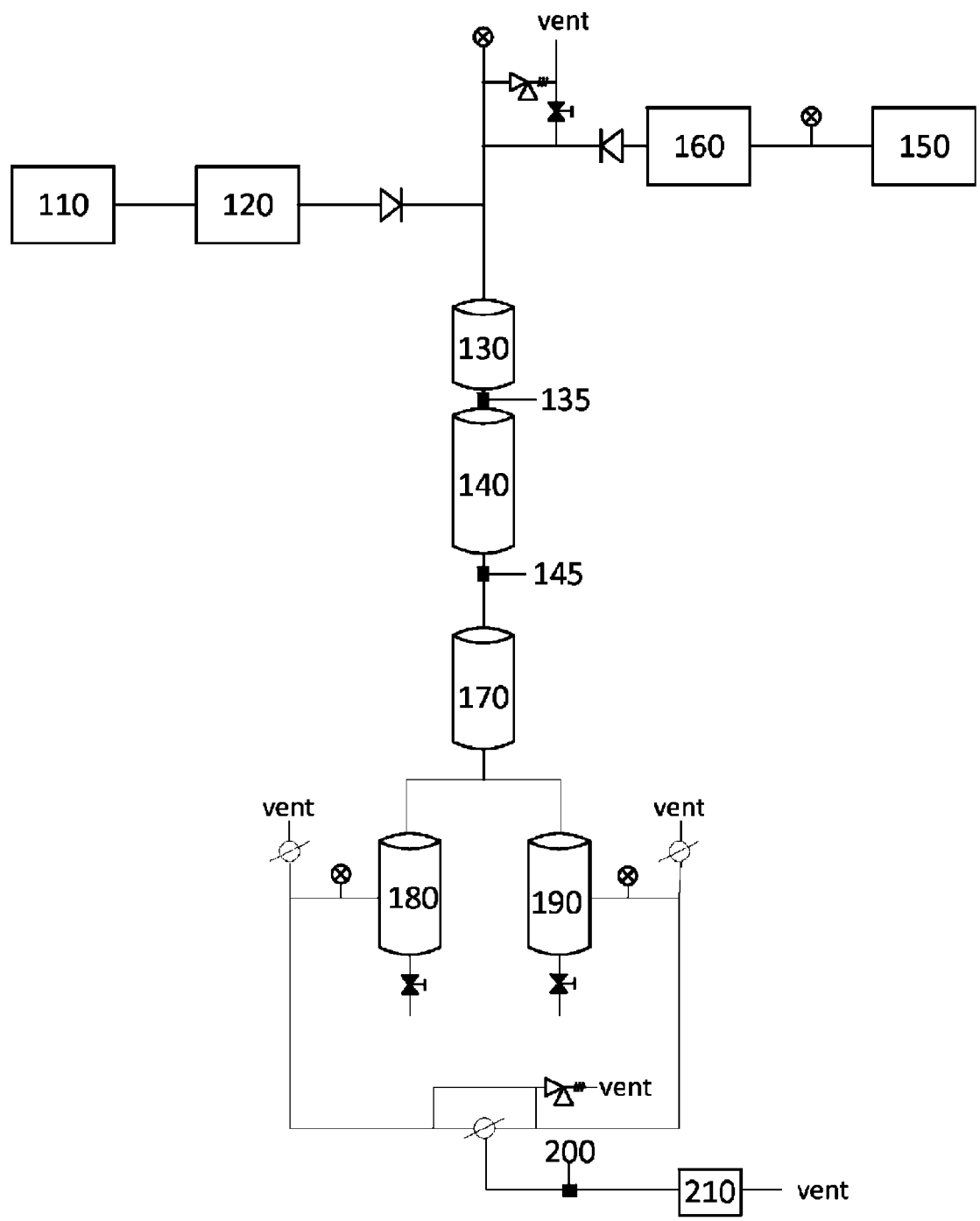
FIG. 2 is a process flow diagram of a continuous, fixed-bed flow reactor, as used in Example 4.

An apparatus similar to that described in Example 3 was used. The process flow diagram is shown in FIG. 2. An isocratic HPLC pump 120 was used to introduce liquid feeds 110, including neat and aqueous BDO. The reactor 140 was made of stainless steel tubing with ¼" outer diameter. The catalyst bed was positioned approximately in the middle of the tube, held in place by quartz wool plugs and 80-100 mesh Pyrex® glass beads, both above (for feed preheating) and below the catalyst bed. The packed reactor tube 140 was placed approximately in the middle of an electrically heated furnace. The furnace control thermocouple 145 was located on the outside skin of the reactor tube, adjacent to the catalyst bed. A preheater 130 and thermocouple were located upstream from the reactor tube 140. A mass flow controller 160 was used to control nitrogen, air, or $H_2$ carrier gases 150 at flow rates up to 1000 sccm. The system also included a condenser 170 and two chilled receiver vessels 180, 190 for collecting liquid product samples alternately without disturbing the run. Effluent gas rates were measured with a soap bubble flow meter 210 and stopwatch and gas samples 200 obtained using a gas-tight syringe. Gas samples were analyzed on a Carle Series 400 AGC using the #160-Sp application (refinery gas analysis). Liquid samples were analyzed on an Agilent 6890 GC with an FID detector or on the Agilent GC/MS described above.

In this example, the catalyst was powdered FZO2089 prepared by MEL Chemicals, Inc. The FZO2089 material is a proprietary mixed oxide preparation of aluminum, lanthanum, and zirconium. A portion of the powdered material was first pelletized, then ground and sieved to a 60-100 mesh size fraction that could be run in the flow reactor. This material had an apparent bulk density of 1.0924 g/cm$^3$ and 0.5472 g (~0.5009 cm$^3$) was loaded into the reactor for testing.

The feedstock solution used was either a 50 wt % solution of BDO (Aldrich) in deionized water or neat BDO (Aldrich). The flow reactor results are shown in Table 36. The highest 1,3BD yields were observed at the lowest reaction temperatures investigated near the end of the testing. It should be noted that a catalyst regeneration step was not implemented during the first 3 runs, but was shown to be beneficial in subsequent runs.

The 1,3BD determinations were based entirely on gas phase analyses, which reported moles of product. Therefore, yields were estimated as a percentage of total BDO fed. Because some 1,3BD was detected in the liquid phase, which was not quantified, the 1,3BD yields reported are considered to be conservative. Estimated yields were lower in the flow reactor than in the pyroprobe. The difference may be attributable to the amount of water in the feed and/or the degree of 1,3BD oligomerization on the catalyst.

TABLE 36

Flow reactor results for the conversion of BDO to 1,3BD

| Run # | Feed Composition | N$_2$ Gas Flow Rate, sccm | Liq. Feed Rate, mL/h | Contact Time, msec | T, °C. | 1,3 BD % Yield |
|---|---|---|---|---|---|---|
| 1 | 50% BDO | 26.0 | 3 | 185 | 450 | 7.93 |
| 2 | 50% BDO | 50.5 | 3 | 126 | 500 | 3.49 |

TABLE 36-continued

Flow reactor results for the conversion of BDO to 1,3BD

| Run # | Feed Composition | N$_2$ Gas Flow Rate, sccm | Liq. Feed Rate, mL/h | Contact Time, msec | T, °C. | 1,3 BD % Yield |
|---|---|---|---|---|---|---|
| 3 | 50% BDO | 26.0 | 3 | 173 | 500 | 3.93 |
| 4* | 50% BDO | 26.0 | 3 | 173 | 500 | 5.74 |
| 5* | Neat BDO | 51.4 | 3 | 189 | 450 | 3.77 |
| 6* | Neat BDO | 50.6 | 3 | 206 | 400 | 8.82 |
| 7* | Neat BDO | 101.6 | 3 | 114 | 400 | 8.33 |

*Catalyst regenerated by heating to 500° C. in air overnight prior to this run

Example 5

Flow Reactor Evaluation of In$_2$O$_3$ Catalysts Prepared by the Ammonium Oxalate Precipitation Method Experiments were conducted using the In$_2$O$_3$ catalyst prepared using the ammonium oxalate method. Testing was conducted in the same apparatus and using the same methods described in Example 3.

Results are shown in Table 37. While the Li-doped material did not have good selectivity, the undoped In$_2$O$_3$ provided MVC selectivities (about 80%) superior to other materials tested and low selectivities to MEK (1-3%). Of the temperatures tested, the highest selectivity was obtained at 300° C. Performance was stable at this temperature for at least 470 min TOS. Doubling the catalyst loading from 0.5 to 1 g increased selectivity to MVC but had a marginal effect on BDO conversion. Note that the blank experiment shows that the reactor tube and pre-heater packing material without any catalyst had a small activity for BDO dehydrogenation at 350° C.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

TABLE 37

Conversion of Neat BDO in a Flow Reactor Using In$_2$O$_3$ Catalysts Synthesized from the Ammonium Oxalate Preparation

| Run | [1]Cat. | Cat. Mass g | MHSV g BDO/ g · cat/hr | Gas Flow mL/ min | W/F, (g · cat)-hr/total mol | T °C. | Tos, min | [2]BDO Conv. % | BD Yield % | BD Sel % | MVC Yield % | MVC Sel % | MEK Yield % | MEK Sel % | Acetoin Yield % | Acetoin Sel % | Mass Bal % | C Bal % |
|---|---|---|---|---|---|---|---|---|---|---|---|---|---|---|---|---|---|---|
| 72 | 10% Li/ In$_2$O$_3$ | 0.5 | 6.00 | 31.7 | 4.5 | 250 | — | 11 | 0.0 | 0.0 | 0.0 | 0.0 | 0.0 | 0.0 | 0.4 | 3.6 | 99 | 91 |
|  |  |  |  |  |  | 300 | — | 13 | 0.0 | 0.0 | 0.0 | 0.0 | 0.4 | 3.1 | 6.0 | 46.2 | 106 | 95 |
|  |  |  |  |  |  | 350 | — | 57 | 0.0 | 0.0 | 0.0 | 0.0 | 2.0 | 3.5 | 23.0 | 40.4 | 98 | 73 |
| 77 | In$_2$O$_3$ | 0.5 | 6.00 | 31.9 | 4.5 | 250 | — | 5 | 0.0 | 0.0 | 3.5 | 69.9 | 0.05 | 1.0 | 0.4 | 7.8 | 105 | 105 |
|  |  |  |  |  |  | 300 | — | 79 | 0.0 | 0.0 | 52.5 | 66.5 | 2.4 | 3.0 | 6.5 | 8.2 | 102 | 91 |
|  |  |  |  |  |  | 350 | — | 100 | 6.2 | 6.2 | 46.8 | 46.8 | 7.1 | 7.1 | 1.1 | 1.1 | 100 | 88 |
| 88 | In$_2$O$_3$ | 0.95 | 3.16 | 31.9 | 8.5 | 250 | — | 16 | 0.0 | 0.0 | 11.1 | 69.4 | 0.0 | 0.0 | 3.0 | 18.8 | 100 | 98 |
|  |  |  |  |  |  | 300 | — | 86 | 3.5 | 4.1 | 64.2 | 74.7 | 3.3 | 3.8 | 9.0 | 10.5 | 101 | 104 |
|  |  |  |  |  |  | 350 | — | 97 | 27.4 | 28.2 | 42.2 | 43.5 | 5.7 | 5.9 | 0.0 | 0.0 | 97 | 102 |
| 91 | In$_2$O$_3$ | 1.01 | 2.97 | 32.2 | 8.9 | 300 | 198 | 71 | 0.0 | 0.0 | 57.6 | 81.1 | 1.1 | 1.5 | 7.7 | 10.8 | 98 | 96 |
|  |  |  |  |  |  |  | 380 | 67 | 0.0 | 0.0 | 54.5 | 81.3 | 1.0 | 1.5 | 7.6 | 11.3 | 98 | 98 |
|  |  |  |  |  |  |  | 470 | 63 | 0.0 | 0.0 | 52.5 | 83.3 | 0.0 | 0.0 | 7.2 | 11.4 | 99 | 97 |
| 98 | None | 0.0 | — | 32.2 | 0.0 | 300 | — | 4 | 0.0 | 0.0 | 0.0 | 0.0 | 0.0 | 0.0 | 0.0 | 0.0 | 98 | 96 |
|  |  |  |  |  |  | 350 | — | 10 | 0.0 | 0.0 | 0.0 | 0.0 | 0.0 | 0.0 | 6.1 | 61.0 | 101 | 96 |

[1]In$_2$O$_3$ by oxalic acid precipitation method
[2]Products were collected in diglyme

We claim:

1. A method, comprising:
converting 2,3-butanediol to methyl vinyl carbinol, 1,3-butadiene, or a mixture thereof by
contacting a feed stream comprising 2,3-butanediol with a catalyst comprising (a) $M_xO_y$ where M is a rare earth metal, a group IIIA metal, Zr, or a combination thereof, and x and y have values based upon an oxidation state of M, and wherein the catalyst is not $CeO_2$, or (b) $M^3{}_a(PO_4)_b$ where $M^3$ is a group IA metal, a group IIA metal, a group IIIA metal, or a combination thereof, and a and b have values based upon the oxidation state of $M^3$; and
dehydrating at least a portion of the 2,3-butanediol to form a product comprising methyl vinyl carbinol, 1,3-butadiene, or a combination thereof.

2. The method of claim 1, wherein the catalyst has a methyl vinyl carbinol selectivity of at least 20%, a 1,3-butadiene selectivity of at least 20%, or a combined 1,3-butadiene and methyl vinyl carbinol selectivity of at least 20%.

3. The method of claim 1, wherein M is In, Sc, La, Tm, or a combination thereof.

4. The method of claim 1, wherein the catalyst further comprises a dopant $M^2$, wherein $M^2$ is a rare earth metal, a group IA metal, a group IIA metal, a group IIIA metal, Zr, or a combination thereof, and wherein $M^2$ is different than M or $M^3$.

5. The method of claim 4, wherein M is Zr.

6. The method of claim 1, wherein the catalyst is (i) an oxide of In, Al, La, and Zr, (ii) an oxide of Al and Zr, (iii) an oxide of Zr and Ca, (iv) $Tm_2O_3$, (v) $ZrO_2$, (vi) $Sc_2O_3$, or (vii) $In_2O_3$.

7. The method of claim 1, wherein the catalyst is $In_2O_3$.

8. The method of claim 1, wherein the feed stream is contacted with the catalyst at a temperature within a range of 250° C. to 700° C. and atmospheric pressure.

9. The method of claim 1, wherein the feed stream is contacted with the catalyst at a flow rate effective to produce a W/F (catalyst weight (g)/feed flow rate (mol/h)) value within a range of 0.5 to 100 g catalyst·h/mol feed stream.

10. The method of claim 9, wherein the W/F value is from 1 to 10 g catalyst·h/mol feed stream.

11. The method of claim 1, wherein at least 5% of the 2,3-butanediol is dehydrated.

12. The method of claim 1, wherein the catalyst is disposed within a column, and the method further comprises flowing the feed stream through the column at a weight hourly space velocity from 0.3 to 12 $h^{-1}$.

13. The method of claim 1, wherein the product comprises methyl vinyl carbinol, and the method further comprises:
contacting the product comprising methyl vinyl carbinol with a solid acid catalyst; and
dehydrating at least a portion of the methyl vinyl carbinol to 1,3-butadiene.

14. The method of claim 13, wherein the solid acid catalyst is an aluminosilicate, alumina, sulfated zirconia, or a mixture thereof.

15. A method, comprising:
converting 2,3-butanediol to 1,3-butadiene by
contacting a feed stream comprising 2,3-butanediol with a first catalyst at a temperature within a range of 250° C. to 700° C., wherein the first catalyst comprises $M_xO_y$ where M is a rare earth metal, a group IIIA metal, Zr, or a combination thereof, and x and y have values based upon an oxidation state of M, and wherein the catalyst is not $CeO_2$;
dehydrating at least 5% of the 2,3-butanediol in the feed stream with the first catalyst to form a first product comprising methyl vinyl carbinol, 1,3-butadiene, or a combination thereof;
contacting the first product with a second catalyst comprising a solid acid catalyst at a temperature from about 250° C. to about 700° C.; and
dehydrating at least 5 wt % of the methyl vinyl carbinol to form a second product comprising 1,3-butadiene.

16. The method of claim 15, wherein M is In, Sc, La, Tm, or a combination thereof.

17. The method of claim 15, wherein the first catalyst further comprises $M^2$, wherein $M^2$ is a rare earth metal, a group IA metal, a group IIA metal, a group IIIA metal, Zr, or a combination thereof, and wherein $M^2$ is different than M.

18. The method of claim 15, wherein the first catalyst is $In_2O_3$.

19. The method of claim 15, wherein at least 50% of the 2,3-butanediol in the feed stream is dehydrated with the first catalyst.

20. The method of claim 19, wherein the solid acid catalyst is an aluminosilicate, alumina, sulfated zirconia, or a mixture thereof.

* * * * *